(12) United States Patent
Zhang et al.

(10) Patent No.: US 10,828,511 B2
(45) Date of Patent: Nov. 10, 2020

(54) SYSTEM AND METHOD FOR OPTIMIZING A TREATMENT PLAN FOR IRRADIATION THERAPY

(71) Applicants: Hao H. Zhang, Potomac, MD (US); Gokhan Kirlik, Baltimore, MD (US); Warren D. D'Souza, Timonium, MD (US); Byong Young Yi, Fulton, MD (US)

(72) Inventors: Hao H. Zhang, Potomac, MD (US); Gokhan Kirlik, Baltimore, MD (US); Warren D. D'Souza, Timonium, MD (US); Byong Young Yi, Fulton, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 18 days.

(21) Appl. No.: 16/324,060

(22) PCT Filed: Aug. 3, 2017

(86) PCT No.: PCT/US2017/045285
§ 371 (c)(1),
(2) Date: Feb. 7, 2019

(87) PCT Pub. No.: WO2018/031365
PCT Pub. Date: Feb. 15, 2018

(65) Prior Publication Data
US 2020/0164225 A1    May 28, 2020

Related U.S. Application Data

(60) Provisional application No. 62/372,492, filed on Aug. 9, 2016.

(51) Int. Cl.
*A61N 5/10*    (2006.01)

(52) U.S. Cl.
CPC ......... *A61N 5/1047* (2013.01); *A61N 5/1031* (2013.01); *A61N 5/1082* (2013.01)

(58) Field of Classification Search
CPC ..... A61B 6/103; A61B 6/1031; A61B 6/1045; A61B 6/1047
See application file for complete search history.

(56) References Cited

U.S. PATENT DOCUMENTS 6,907,105 B2    6/2005   Otto
7,162,008 B2 *  1/2007   Earl ..................... A61N 5/1031
                                                         378/149

(Continued)

OTHER PUBLICATIONS

Craft et al., Multicriteria VMAT optimization, Medical Physics, 2012, pp. 686-696, vol. 39.

(Continued)

*Primary Examiner* — Thomas R Artman
(74) *Attorney, Agent, or Firm* — Wolter Van Dyke Davis, PLLC; Eugene J. Molinelli

(57) ABSTRACT

A method and apparatus is presented for optimizing a treatment plan for irradiation therapy. The method includes determining voxels in a reference frame of a radiation source that rotates at an angular rate of change and emits a beam at a plurality of angles. The beam has a beam intensity and a cross sectional shape based on an aperture of a collimator at each angle. The method includes determining an initial aperture value at each angle and minimizing a single objective function subject to a constraint on an aperture rate of change to determine an aperture and beam intensity at each angle. The method also includes delivering a beam of radiation with controlled intensity at each angle based on the beam intensity and aperture and turning the beam of radiation off at an intervening angle not included in the plurality of angles.

25 Claims, 23 Drawing Sheets

(56) References Cited

U.S. PATENT DOCUMENTS

| | | | |
|---|---|---|---|
| 7,333,591 B2* | 2/2008 | Earl | A61N 5/1031 378/149 |
| 7,773,723 B2* | 8/2010 | Nord | G16H 20/40 378/65 |
| 7,835,494 B2* | 11/2010 | Nord | G16H 20/40 378/65 |
| 7,880,154 B2 | 2/2011 | Otto | |
| 7,907,987 B2 | 3/2011 | Dempsey | |
| 8,254,521 B2 | 8/2012 | Brooks et al. | |
| 8,663,084 B2* | 3/2014 | Bzdusek | A61N 5/103 128/897 |
| 9,687,677 B2* | 6/2017 | Otto | A61N 5/107 |
| 9,687,678 B2* | 6/2017 | Otto | A61B 5/08 |
| 9,737,730 B2* | 8/2017 | Cheng | A61N 5/1047 |
| 10,556,124 B2* | 2/2020 | Zhang | A61N 5/1039 |
| 2004/0071261 A1* | 4/2004 | Earl | A61N 5/1047 378/65 |
| 2007/0064871 A1* | 3/2007 | Earl | A61N 5/1047 378/65 |
| 2010/0051824 A1* | 3/2010 | Nord | G06Q 50/22 250/395 |
| 2010/0054410 A1* | 3/2010 | Nord | G06Q 50/22 378/65 |
| 2010/0219356 A1* | 9/2010 | Bzdusek | A61N 5/1047 250/492.1 |
| 2014/0357931 A1* | 12/2014 | Cheng | A61N 5/1047 600/1 |
| 2017/0246477 A1* | 8/2017 | Zhang | A61N 5/1031 |
| 2020/0164225 A1* | 5/2020 | Zhang | A61N 5/1031 |

OTHER PUBLICATIONS

Unkelbach et al., Optimization approaches to volumetric modulated arc therapy planning, Medical Physics, 2015, pp. 1367-1377, vol. 42.

Ehrgott et al., Mathematical optimization in intensity modulated radiation therapy, Annals of Operations Research, 2010, pp. 309 365, vol. 175.

Romeijn et al., A novel linear programming approach to fluence map optimization for intensity modulated radiation therapy treatment planning, Physics in Medicine and Biology, 2003, pp. 3521-3542, vol. 48.

Naqvi et al., Convolution/superposition using the Monte Carlo method, Phys. Med. Biol., 2003, pp. 2101-2121, vol. 48.

International Search Report and Written Opinion, International Patent Application No. PCT/US2017/045285, dated Oct. 23, 2017.

* cited by examiner

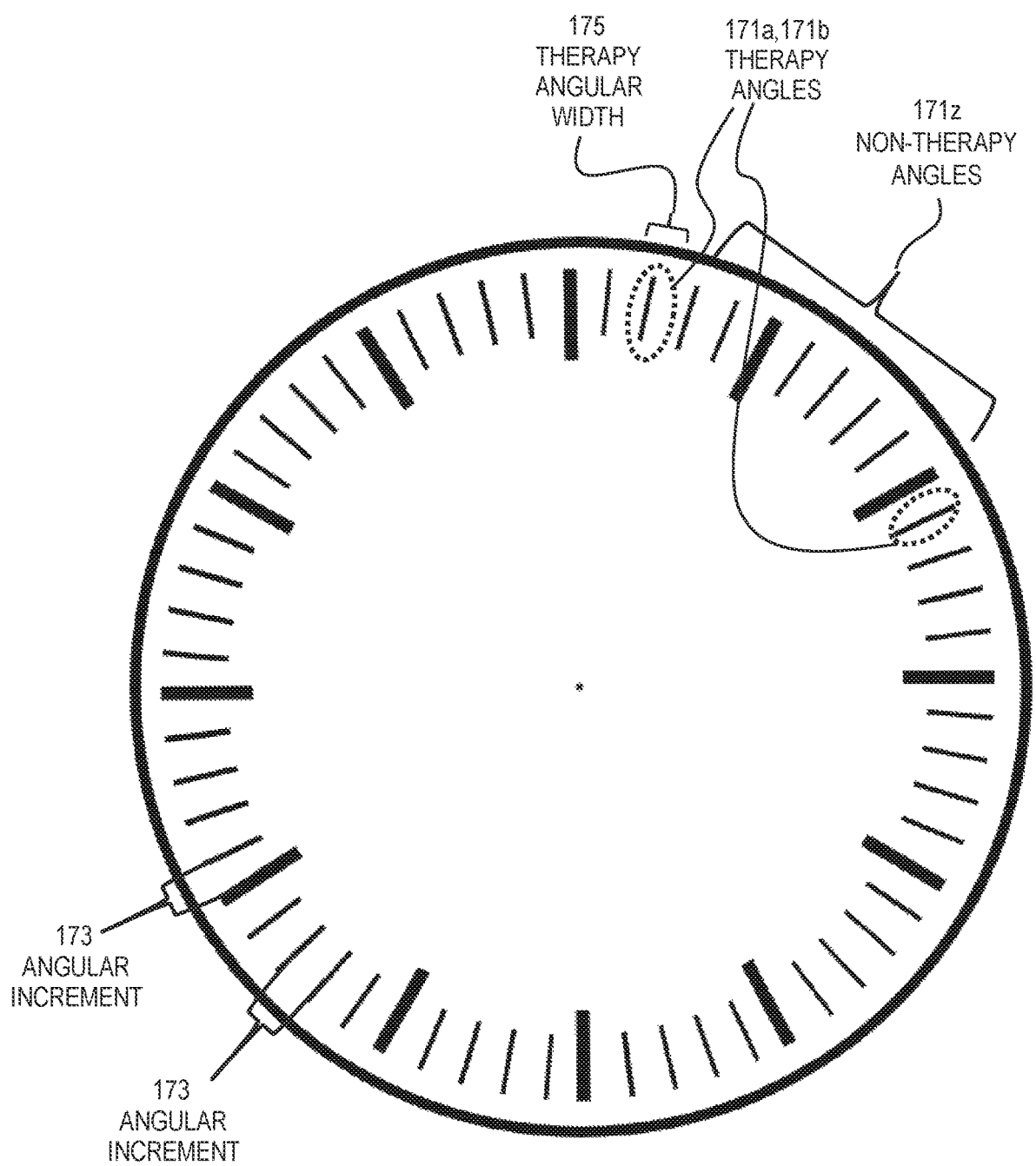

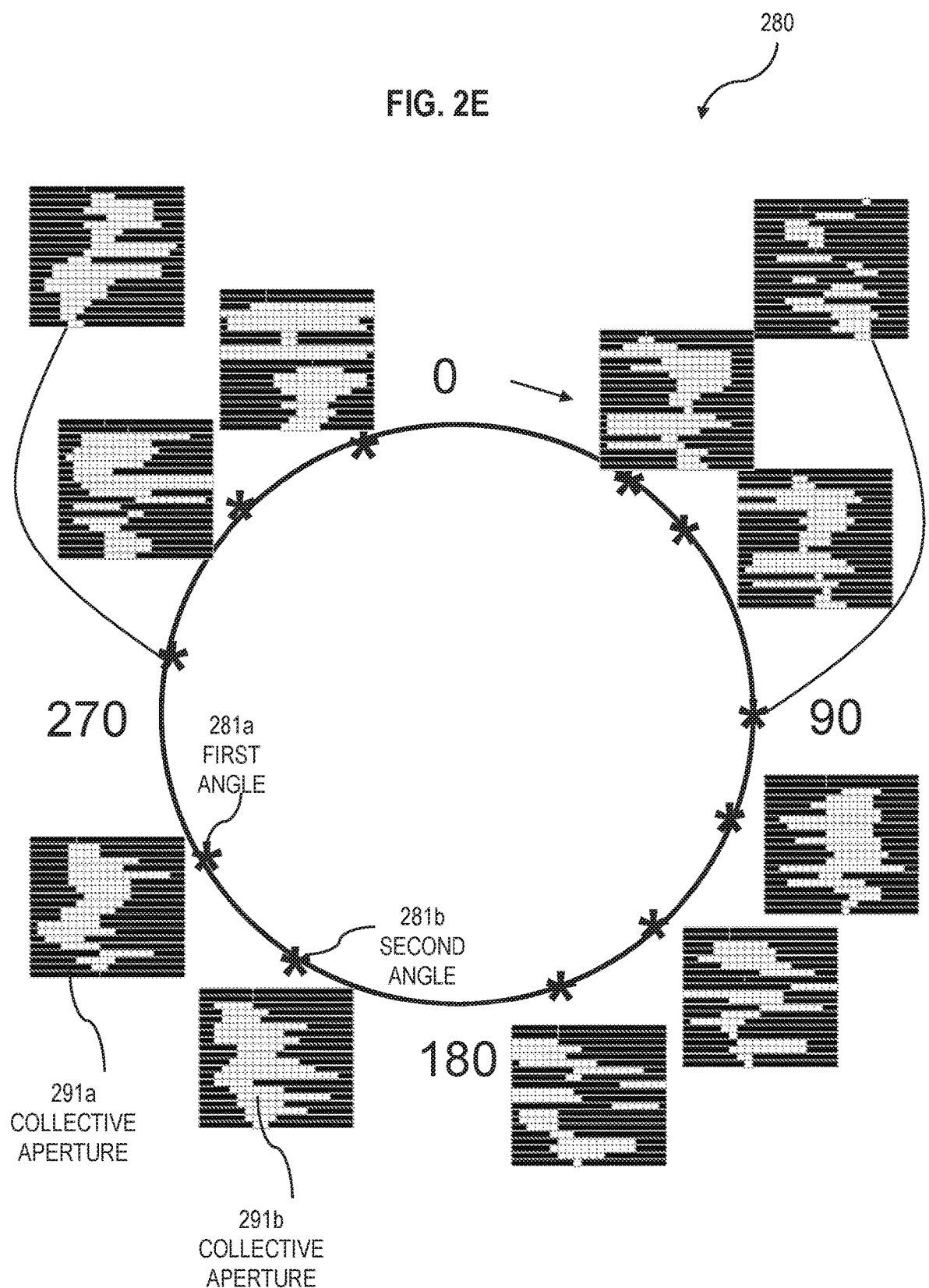

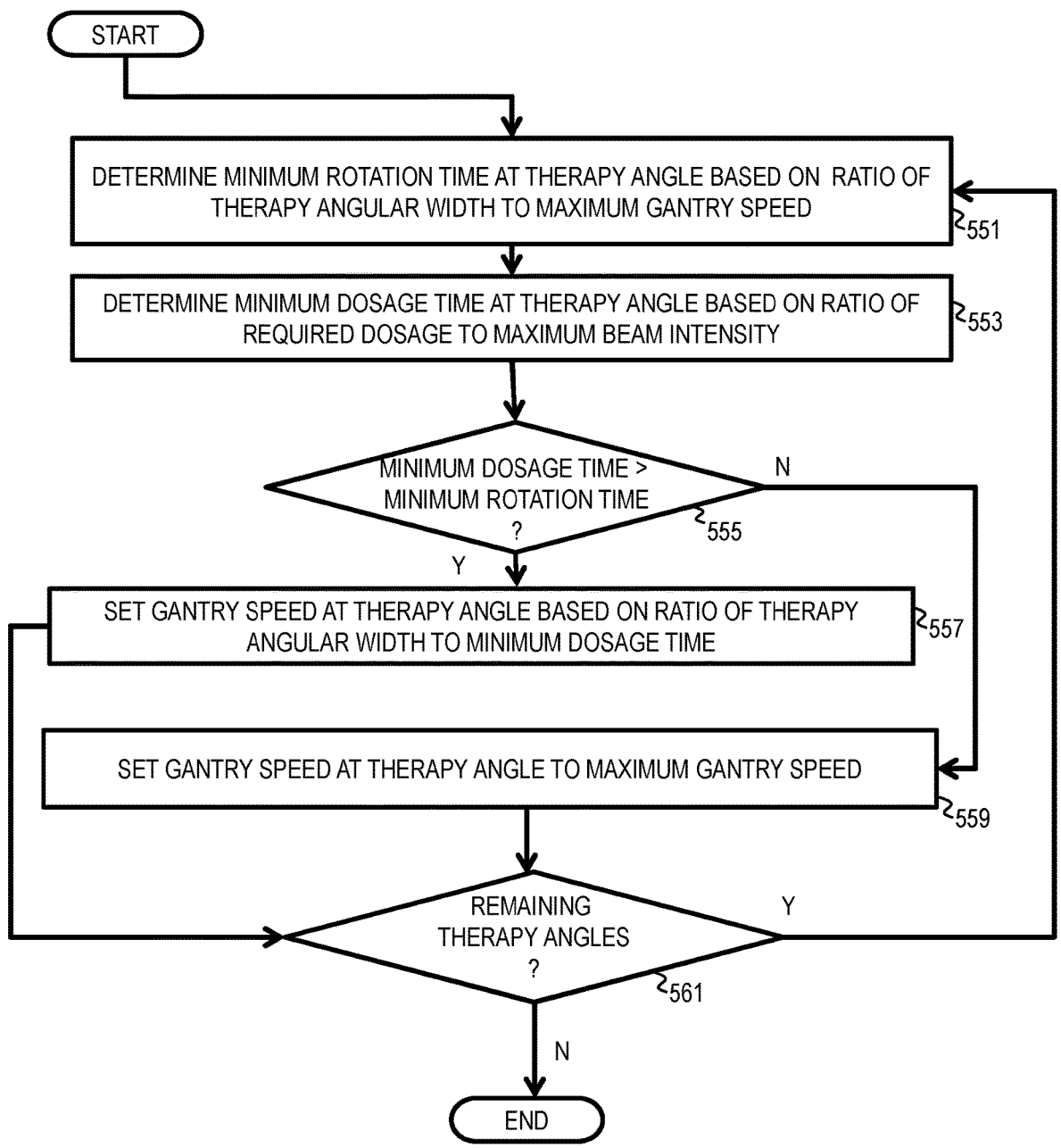

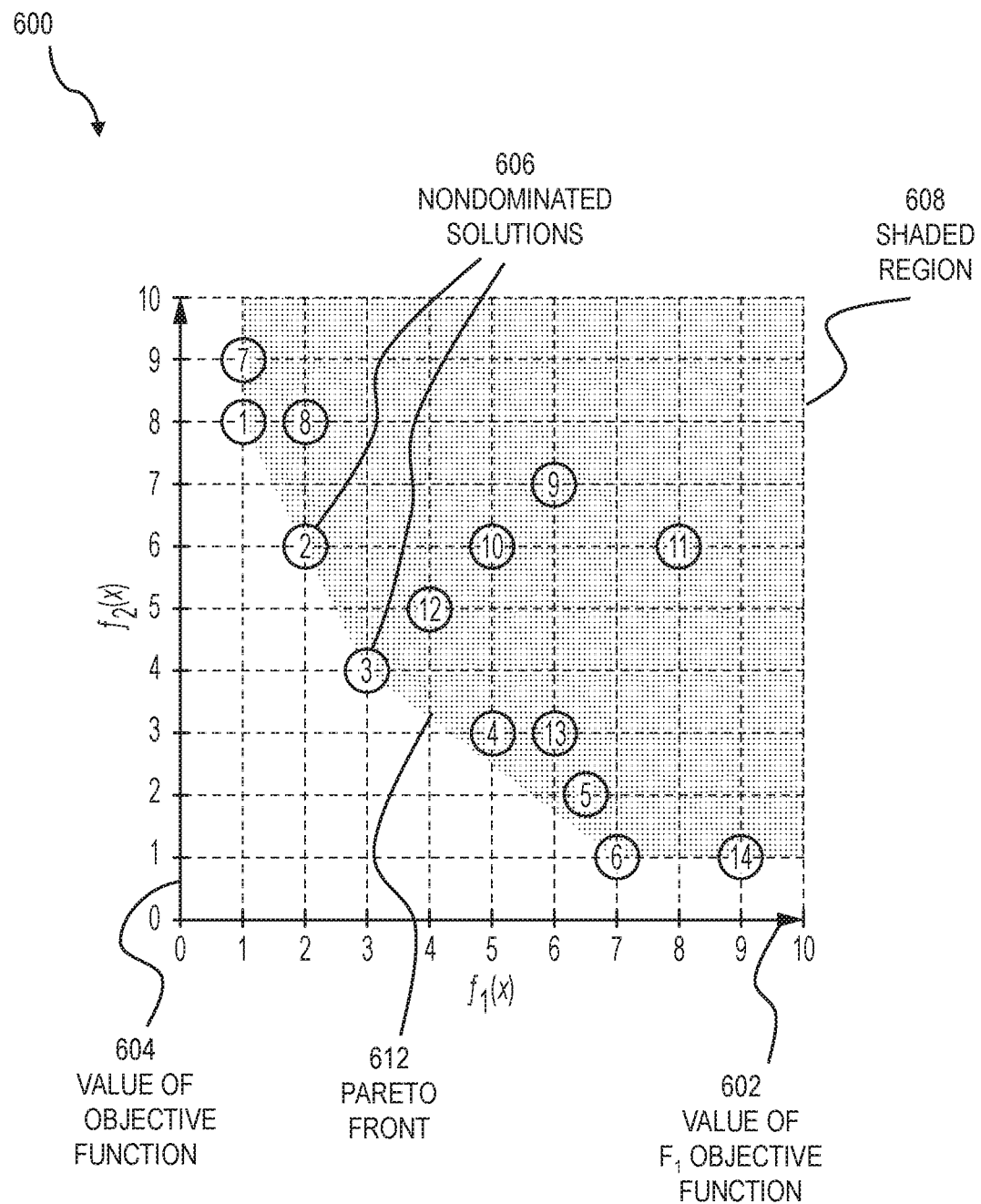

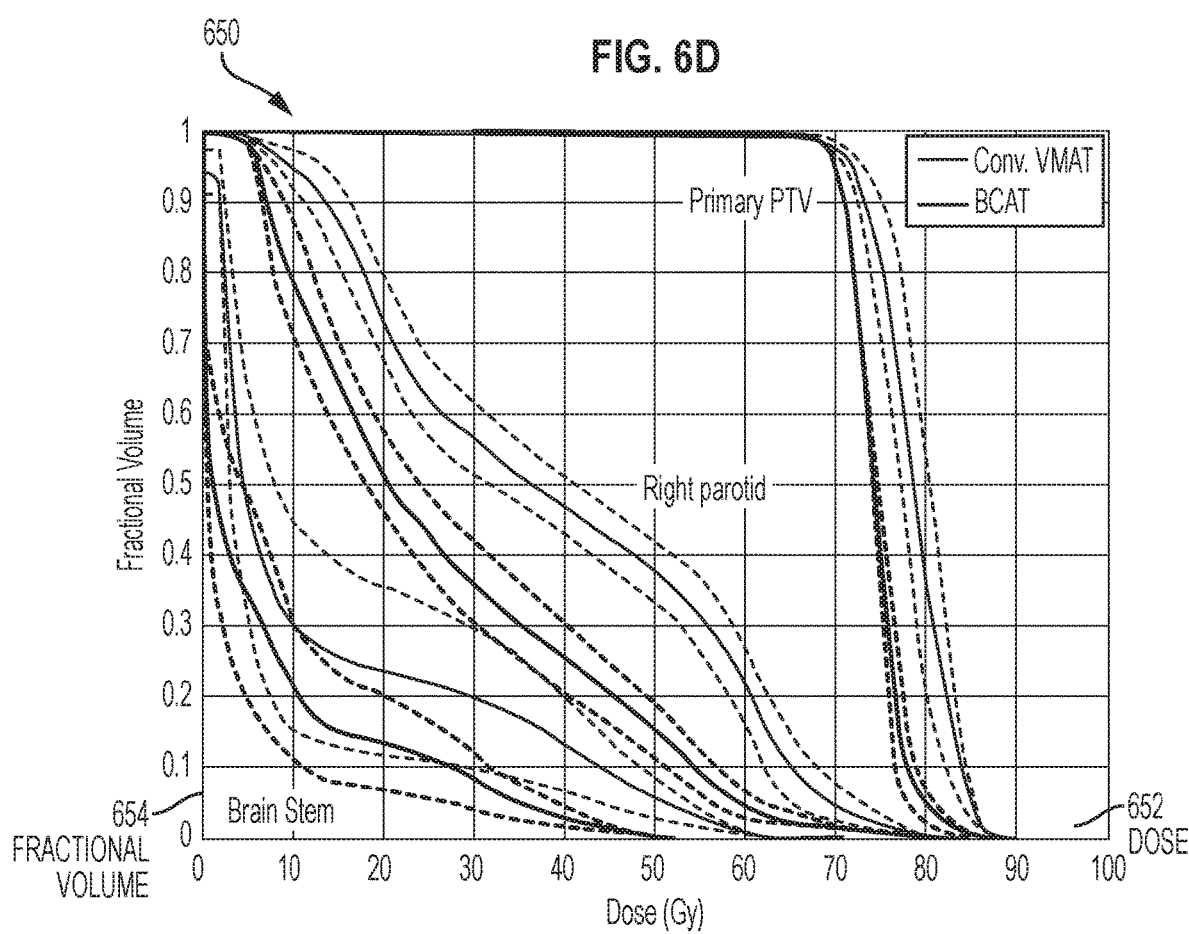

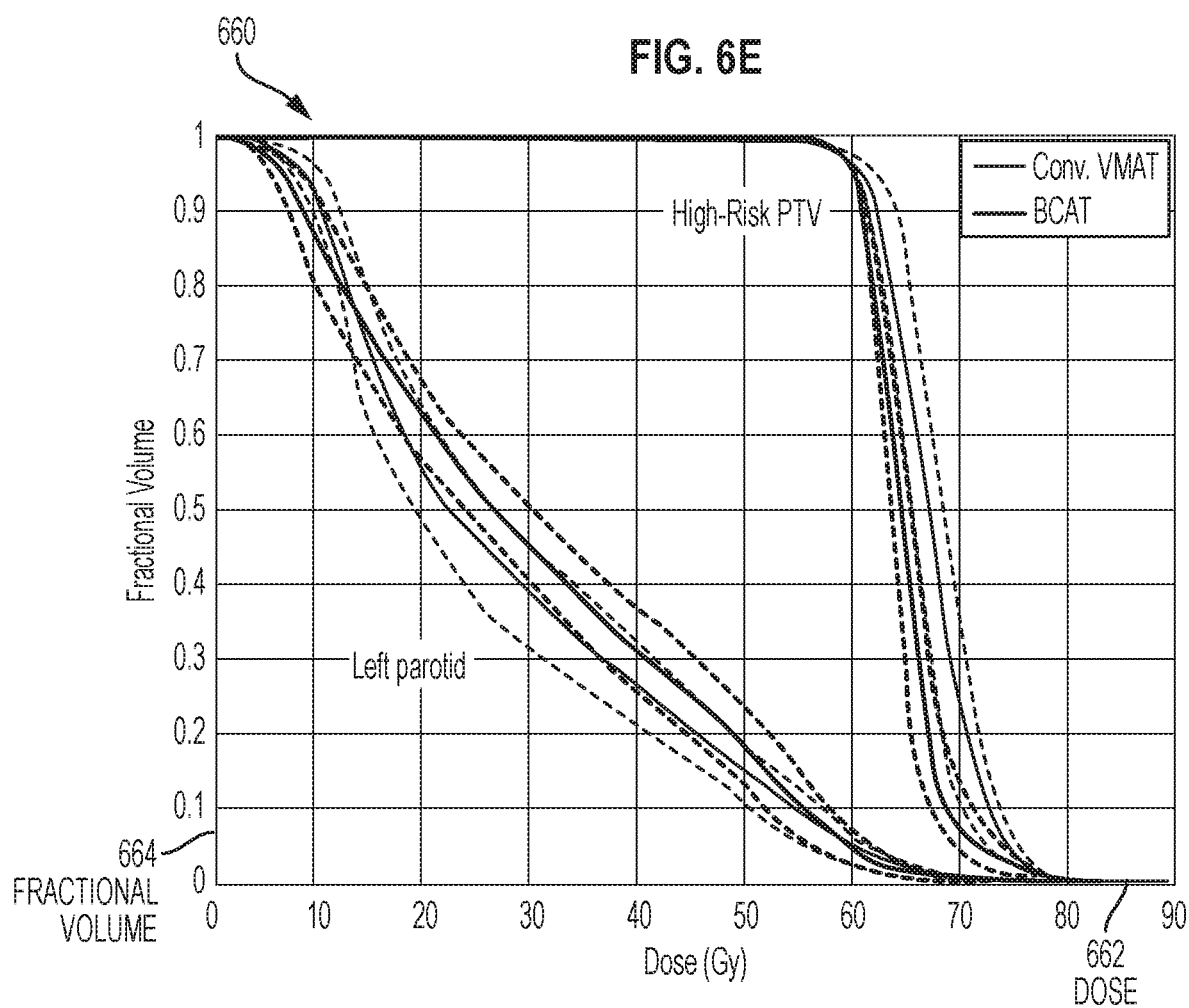

SYSTEM AND METHOD FOR OPTIMIZING A TREATMENT PLAN FOR IRRADIATION THERAPY

CROSS-REFERENCE TO RELATED APPLICATION

This application is a 371 national state application of PCT Application No. PCT/US17/45285, filed Aug. 3, 2017, and claims benefit of Provisional Appln. 62/372,492, filed Aug. 9, 2016, the entire contents of each of which are hereby incorporated by reference as if fully set forth herein, under 35 U.S.C. § 119(e).

BACKGROUND

Radiotherapy is a treatment for cancer patients involving the use of high-energy radiation. When high-energy radiation is delivered to a subject, it kills cells in the body. Although the high-energy radiation kills tumor cells in the subject's body, it may also kill normal tissue cells and tissue cells of an organ-at-risk (OAR) that surround the tumor. Thus, the goal of conventional radiotherapy is to deliver a sufficient radiation dose to the tumor to kill the tumor cells while minimizing the radiation dose delivered to the normal tissue cells and OAR tissue cells that surround the tumor.

SUMMARY

It is here recognized that conventional methods for optimizing irradiation therapy, such as Volumetric-Modulated Arc Therapy (VMAT) are deficient, since they continuously rotate the gantry around the subject while the beam is on. Some of the angles may not contribute to or may even deteriorate the plan quality. As a result, the treatment plan generated by conventional VMAT methods leaves the beam on at angles that introduce quality degradation to the plan.

In a first set of embodiments, a method is provided for optimizing a treatment plan for irradiation therapy. The method includes determining a plurality of voxels in a reference frame of a radiation source that rotates at an angular rate of change based on a gantry speed. The radiation source emits a beam of radiation at a plurality of angles with controlled intensity based on a beam intensity value and beam cross sectional shape at each angle based on a value of an aperture of a collimator positioned between the radiation source and a subject. The method further includes determining an initial aperture at each angle of a plurality of initial angles. The method further includes minimizing a single objective function that is based on the gantry speed and beam intensity subject to a constraint on an aperture rate of change based on an adjustment speed of the collimator using the initial aperture and an initial beam intensity value at each angle of the plurality of initial angles to determine the beam intensity and aperture at each angle. The method further includes delivering the beam of radiation with controlled intensity and beam cross sectional shape at each angle using the beam intensity and the aperture and turning the beam off at intervening angles not included in the plurality of angles.

In some embodiments of the first set, the method further includes determining for a new angle other than the plurality of initial angles an aperture and a beam intensity value based on a radiation dose delivered to the voxels. In some of these embodiments, the method further includes minimizing the single objective function subject to the constraint on the aperture rate of change and a constraint on the angular rate of change using the apertures and beam intensity values at the plurality of angles and the new angle such that the value of the single objective function is reduced from the value using the plurality of angles without the new angle and the new angle is added to the plurality of angles.

In a second set of embodiments, a computer-readable medium carrying one or more sequences of instructions is provided, where execution of the one or more sequences of instructions by one or more processors causes the one or more processors to perform one or more steps of the above method, or an apparatus or system is configured to perfume one or more steps of the above method.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 1E is a block diagram that illustrates an example of a plurality of therapy angles and non-therapy angles over an arc of the system of FIG. 1D, according to an embodiment;

FIG. 2E is a block diagram that illustrates an example of a conventional system for optimizing a treatment plan for irradiation therapy;

FIG. 5B is a flow diagram that illustrates an example of a method for determining a gantry speed at each therapy angle in a treatment plan for irradiation therapy, according to an embodiment;

FIG. 6A is a graph that illustrates an example of multiple solutions to the optimizing of a treatment plan with two objective functions, according to an embodiment;

FIG. 6D is a graph that illustrates an example of fractional volume versus dosage for a target volume, an organ-at-risk and a critical organ, according to an embodiment;

FIG. 6E is a graph that illustrates an example of fractional volume versus dosage for a target volume and an organ-at-risk, according to an embodiment;

DETAILED DESCRIPTION

A method and apparatus are described for optimizing a treatment plan for irradiation therapy where the radiation source continuously moves through an arc around a subject without stopping and the beam is turned on and off at various angles around the arc to optimize the treatment plan. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of optimizing treatment plans for irradiation therapy of tumors of the head and neck. However, the invention is not limited to this context. In other embodiments, other targets of external radiation therapy using other radiation sources in other regions of a human or non-human subject are subjected to radiation.

1. OVERVIEW

Figure 1A:
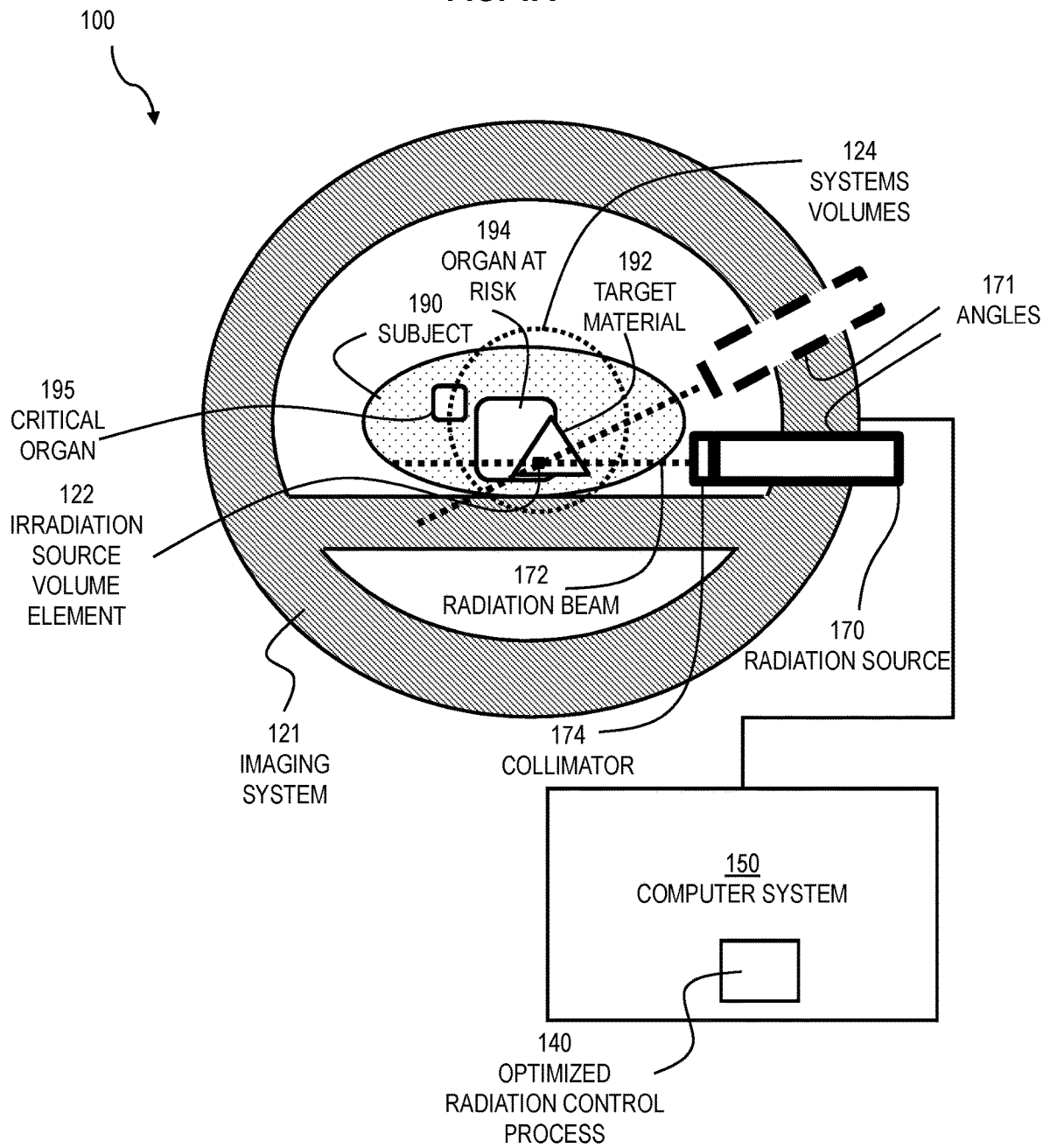
FIG. 1A is a block diagram that illustrates an example system for optimizing a treatment plan for irradiation therapy, according to an embodiment.

FIG. 1A is a block diagram that illustrates an example system 100 for optimizing a treatment plan for irradiation therapy, according to an embodiment. For purposes of illustration, a living subject 190 is depicted, but is not part of the system 100. Zero or more imaging systems 121 are provided, to image the subject 190 within a systems volume 124 that encompasses part of the subject 190. In some embodiments, the volume 124 may encompass the entire subject 190. The imaging systems 121 are external and direct low energy imaging radiation into the volume 124 of the subject 190. In an example embodiment, the imaging systems 121 obtain first measurements that relate to tissue type inside the volume 124. For example, the imaging system 121 is an X-ray Computed tomography (CT) scanner or a nuclear magnetic resonance imagery (MRI) scanner.

As illustrated in FIG. 1A, a target material 192 indicated by a triangle is positioned within the subject 190. In an example embodiment, the target material 192 includes tumor cells. Additionally, an organ-at-risk (OAR) 194 is positioned within the subject 190. Additionally, a critical organ 195 is positioned within the subject 190. The region of the volume 124 that is not occupied by the target material 192, the OAR 194 and the critical organ 195 is occupied by tissues in a category called normal tissue.

As illustrated in FIG. 1A, the system 100 includes a radiation therapy device including a collimator 174 and radiation source 170 that emits a high energy, ionizing beam 172 that penetrates the volume 124 over a plurality of volume elements or voxels 122 that are defined within a frame of reference of the radiation source 170. The radiation source 170 transmits the beam 172 through the collimator 174 to the voxels 122 within the volume 124. The dose at each voxel 122 is dependent on the beam 172 intensity and aperture shapes (not shown) of the collimator 174. Combining the effects of multiple beams (their intensities and shapes), the goal is to transmit a high dose to the target material 192 sufficient to damage or kill cells in that target material 192, and a low dose to the normal tissue, the critical organ 195 and the OAR 194.

During operation of the system 100, the radiation source 170 rotates through a plurality of angles 171 around the subject 190, so that the beam 172 is directed at the target material 192 from multiple angles 171. At each angle the beam intensity and aperture of the collimator may change from those values at other angles, and multiple different intensity and aperture may be used at the same angle.

Although FIG. 1A depicts the radiation source 170 rotated through two angles 171, in one embodiment, the radiation source 170 is rotated through more than two angles 171 around the entire subject 190. Two kinds of radiation therapy are in common use. One type stops the radiation source at each of multiple angles and irradiates the subject at each angle through one or more sets of apertures. In an example embodiment, this type of radiation source stops at between 5-9 angles and irradiates the subject at each angle. This kind of therapy is called Intensity Modulated Radiation Therapy (IMRT). FIG. 2D is a block diagram that illustrates an example of a conventional system 250 for optimizing a treatment plan for irradiation therapy using IMRT. While moving through an arc 252, the radiation source stops at a plurality of angles 271a, 271b and irradiates the subject at each angle 271a, 271b based on the aperture values of the collimator (not shown) at each angle. Since the radiation source stops at each angle 271a, 271b, the collimator has more time to adjust to a particular aperture value and thus this system permits a flexible range of aperture values to be used at each angle.

Another type of conventional radiation therapy does not stop at any of the angles for applying a dose; but, instead, spreads the dose over one or more angular increments. This kind of therapy is called volumetric modulated arc therapy (VMAT). FIG. 2E is a block diagram that illustrates an example of a conventional system 280 for optimizing a treatment plan for irradiation therapy using VMAT. The radiation source continuously moves through an arc, including from a first angle 281a to a second angle 281b. At the first angle 281a, the radiation source irradiates the subject based on an aperture 291a formed by the collimator and at the second angle 281b, the radiation source irradiates the subject based on an aperture 291b formed by the collimator. As the radiation source continuously moves between the angles 281a, 281b, the radiation source continuously illuminates the subject while the collimator simultaneously transitions from the aperture 291a to the aperture 291b. VMAT has the advantage of speeding the delivery of effective doses, but the disadvantage of irradiating the subject at non-optimal angles (e.g. at one or more intervening angles between the angles 281a, 281b) with non-optimal apertures (e.g. at one or more apertures between aperture 291a and aperture 291b) and non-optimal intensities.

In IMRT, at each angle 171, the radiation source 170 is stopped and irradiates the voxels 122 within the volume 124 with the beam 172 having a specific intensity and shape based on apertures of the collimator 174. The process may be repeated for multiple apertures and intensities. In VMAT, if the aperture and intensity do not change too much from one angle to the next, then the radiation source 170 can continuously rotate around the subject 190 without stopping. The improvements described herein to VMAT includes allowing the intensity of the beam to vary at each angle and turning the beam off at one or more intervening angles (e.g. at one or more angles between angles 281a, 281b); and, the process is referenced herein as beam-controlled arc therapy (BCAT).

At some angles 171 of the radiation source 170, the beam 172 needs to pass through the OAR 194 to get to the target material 192. As illustrated in FIG. 1A, when the radiation source 170 rotates to an angle 171 on a left side of the target material 192, the beam 172 needs to pass through the OAR 194 to get to the target material 192. However, at other angles 171 of the radiation source 170, the beam 172 need not pass through the OAR 194 to get to the target material 192. As illustrated in FIG. 1A, when the radiation source 170 rotates to an angle 171 at a top side of the target material 192, the beam 172 need not pass through the OAR 194 to get to the target material 192.

Figure 7:
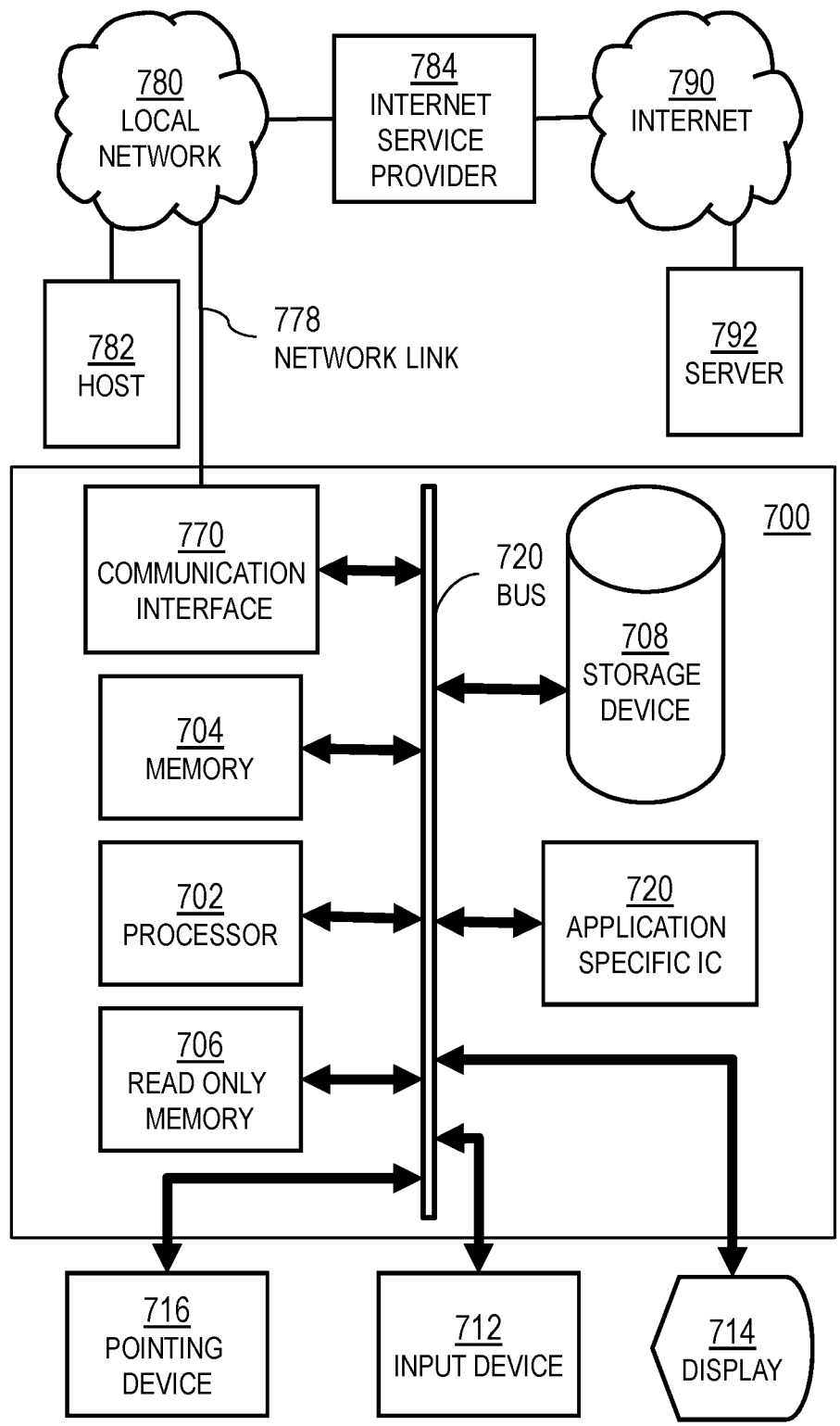
FIG. 7 is a block diagram that illustrates a computer system upon which an embodiment of the invention may be implemented.
Figure 8:
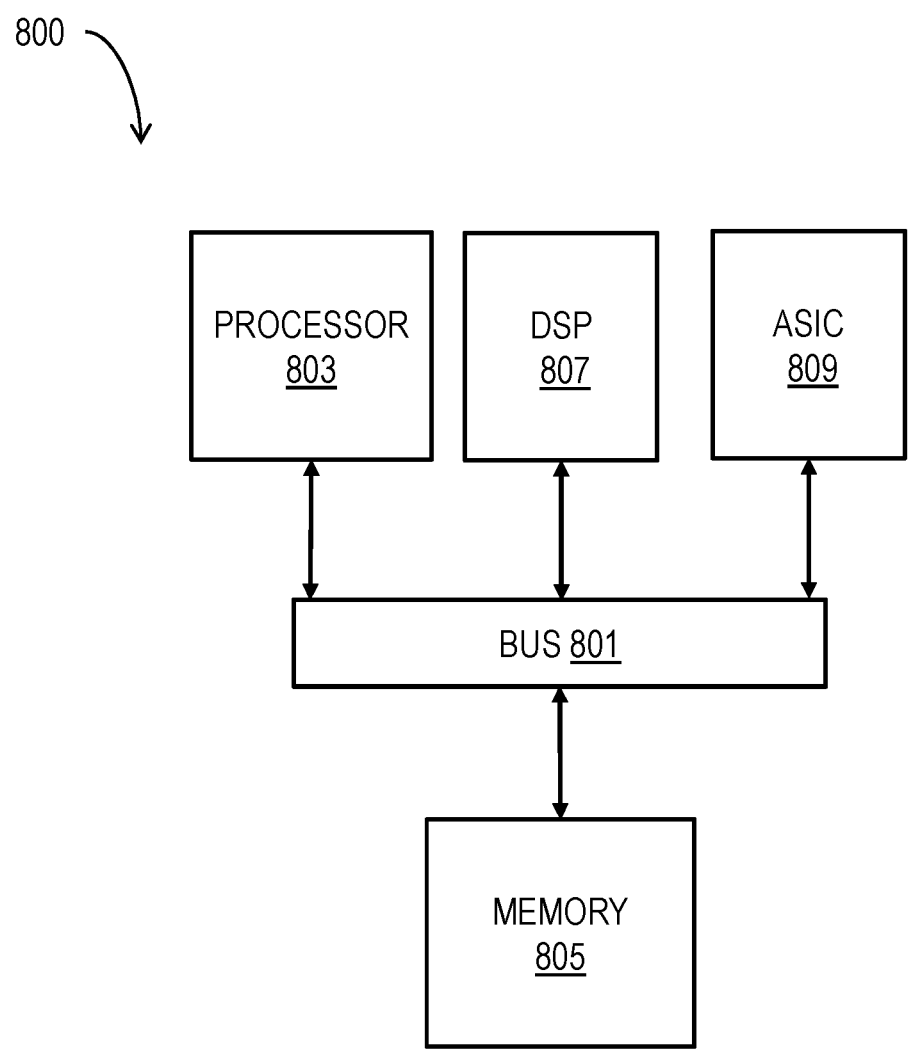
FIG. 8 is a block diagram that illustrates a chip set upon which an embodiment of the invention may be implemented.

As illustrated in FIG. 1A, a computer system 150 is provided to control the one or more imaging system 121, to collect imaging data from the one or more imaging system 121, and to determine a treatment plan including aperture values of the collimator 174 and intensity of the radiation source 170 at each angle 171. The computer system 150 includes an optimized radiation control process 140 to perform one or more steps of a method described below with reference to FIG. 5A. In various embodiments, the computer system 150 comprises one or more general purpose computer systems, as depicted in FIG. 7 or one or more chip sets as depicted in FIG. 8, and instructions to cause the computer or chip set to perform one or more steps of a method described below with reference to FIG. 5A.

Figure 1B:
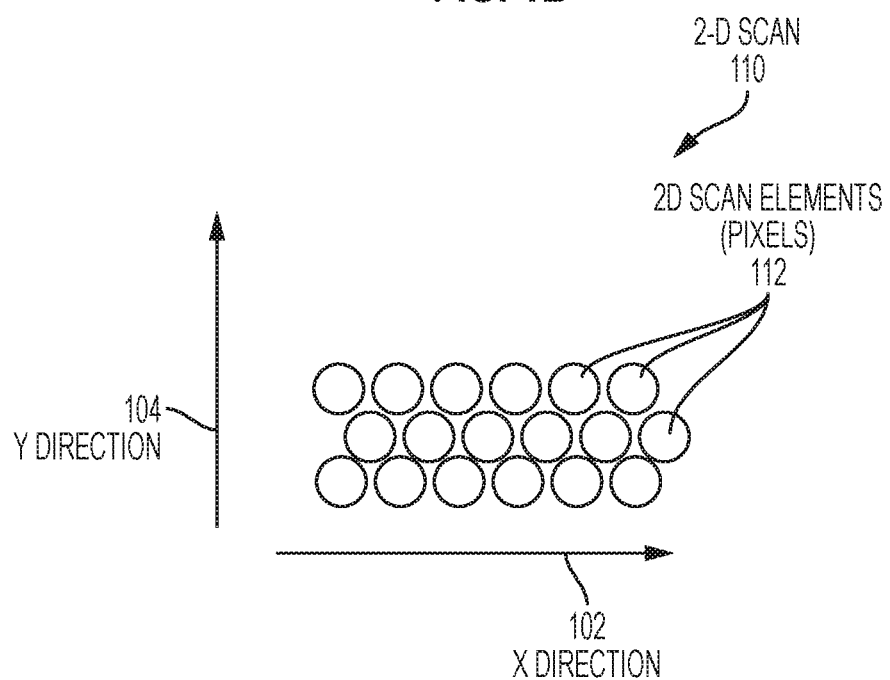
FIG. 1B is a block diagram that illustrates scan elements in a 2D scan, such as one scanned image from a CT scanner.

FIG. 1B is a block diagram that illustrates scan elements in a 2D scan 110, such as one scanned image of the volume 124 from the imaging system 121, such as a CT scanner. The two dimensions of the scan 110 are represented by the x direction arrow 102 and the y direction arrow 104. The scan 110 consists of a two dimensional array of 2D scan elements (pixels) 112 each with an associated position. Typically, a 2D scan element position is given by a row number in the x direction and a column number in the y direction of a rectangular array of scan elements. A value at each scan element position represents a measured or computed intensity or amplitude that represents a physical property (e.g., X-ray absorption, or resonance frequency of an MRI scanner) at a corresponding position in at least a portion of the spatial arrangement of the living body. The measured property is called amplitude hereinafter and is treated as a scalar quantity. In some embodiments, two or more properties are measured together at a pixel location and multiple amplitudes are obtained that can be collected into a vector quantity, such as spectral amplitudes in MRSI. Although a particular number and arrangement of equal sized circular scan elements 112 are shown for purposes of illustration, in other embodiments, more elements in the same or different arrangement with the same or different sizes and shapes are included in a 2D scan.

Figure 1C:
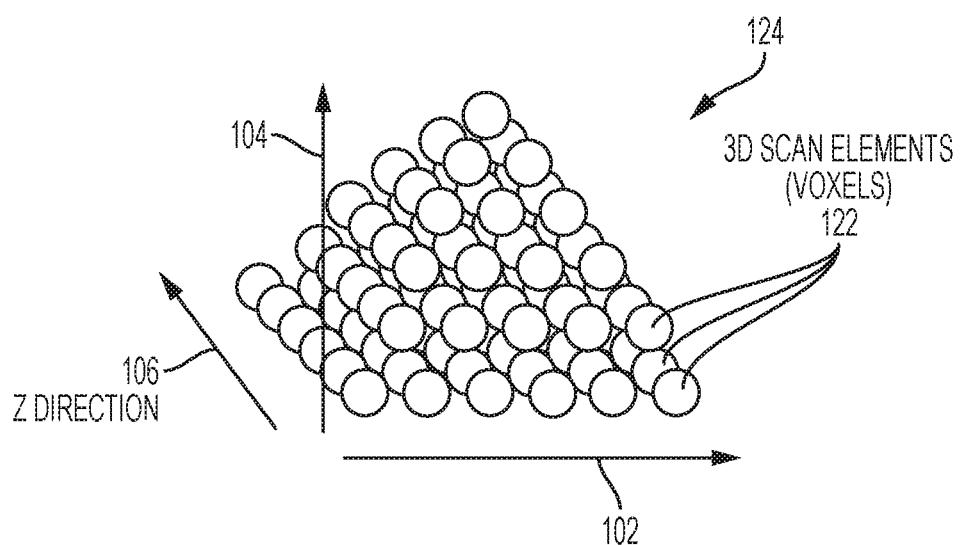
FIG. 1C is a block diagram that illustrates a plurality of voxels within a fixed frame of reference of the radiation source of FIG. 1A.

FIG. 1C is a block diagram that illustrates the plurality of voxels 122 that are defined in the volume 124 within a fixed frame of reference of the radiation source 170 of FIG. 1A. The fixed frame of reference of the radiation source 170 is defined based on the x-direction 102, y-direction 104 and z-direction 106. Thus, in an example embodiment, a particular voxel 122 within the volume 124 in the frame of reference of the radiation source 170 is assigned a unique x-value, y-value and z-value. As previously discussed, some of the voxels 122 are occupied by target material 192, some of the voxels 122 are occupied by OAR material 194, some of the voxels 122 are occupied by critical organ material 195 and the remaining voxels 122 in the volume 124 are occupied by normal tissue material. The computer system 150 determines aperture values of the collimator 174 at each angle 171 which determine the respective intensity of the beam 172 at each voxel 122. Although a particular number and arrangement of equal voxels 122 are shown for purposes of illustration, in other embodiments, more voxels 122 in the same or different arrangement with the same or different sizes and shapes are included in the frame of reference of the radiation source 170. In an example embodiment, the voxel 122 has a length in a range of 3-5 millimeters, a width in a range of 3-5 millimeters and a depth in a range of 2-3 millimeters.

Figure 1D:
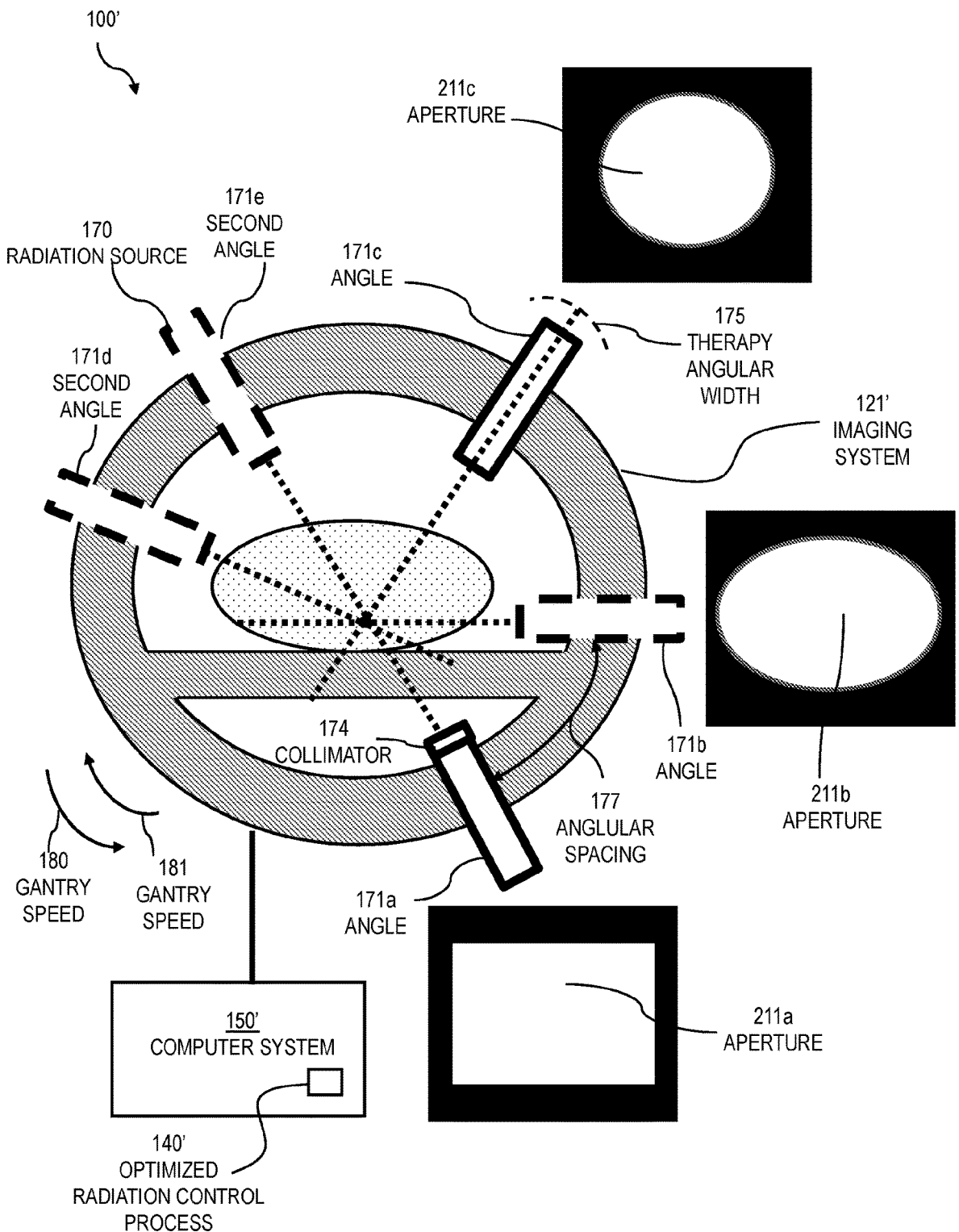
FIG. 1D is a block diagram that illustrates an example system for optimizing a treatment plan for irradiation therapy, according to an embodiment.
Figure 2A:
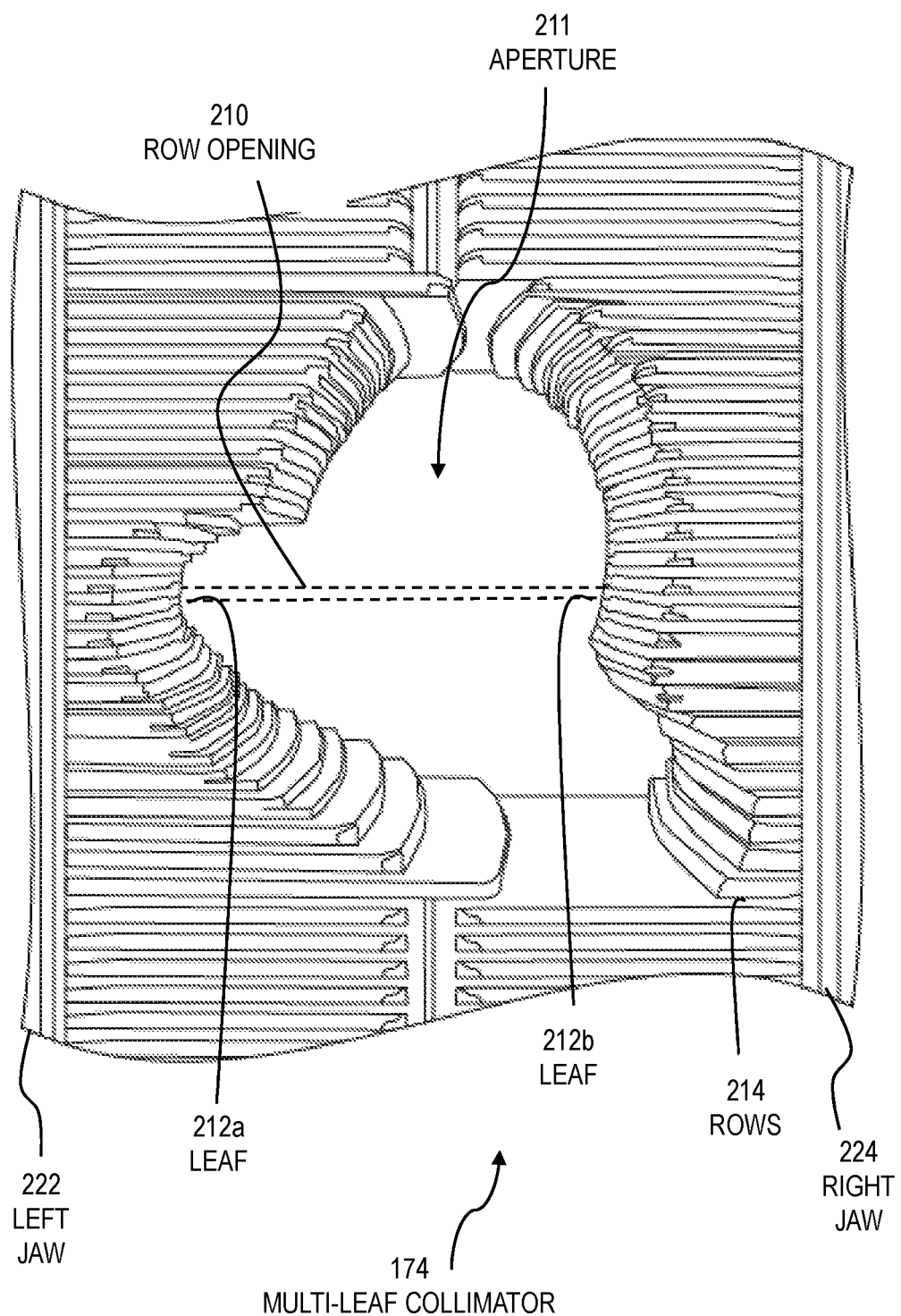
FIG. 2A is an image that illustrates an example of a multi-leaf collimator (MLC) used in the system of FIG. 1A, according to an embodiment.

FIG. 2A is an image that illustrates an example of a multi-leaf collimator (MLC) used as collimator 174 in the system of FIG. 1, according to an embodiment. The MLC 174 is positioned between the radiation source 170 and the subject 190 at each angle 171. In an embodiment, the MLC 174 is coupled to the radiation source 170 and rotates through each angle 171 with the radiation source 170. A surface area of the MLC 174 is divided into a plurality of rows 214. A plurality of row openings 210 in each respective row 214 are formed by selectively moving metal leaves 212a and 212b (collectively referenced hereinafter as leaves 212) within the rows 214 by a controller, e.g., by control process 140 or 140' on a computer processor. In some embodiments, the leaves 212 are called MLC leaves. The row opening 210 within each respective row 214 is defined as having a width equal to a width of the metal leaves 212 and having a length equal to a distance between a tip of a left leaf 212a in the row 214 extending from a left jaw 222 of the MLC 174 and a tip of a right leaf 212b in the row 214 extending from a right jaw 224 of the MLC 174. The collection of row openings 210 among all rows 214 forms a two-dimensional arbitrary shape called an aperture 211.

Each row opening 210 is divided into one or more beamlets or area elements. A value of each beamlet (such as a square area element of length and width equal to the row width) within each row opening 210 within the aperture 211 is either 0 (closed) or 1 (open). A 2D array of beamlet values for all of the row openings 210 making up the aperture 211 is referred to as aperture values. In the embodiment, a value of 0 corresponds to the beamlet of the row opening being a closed space occupied by metal leaves 212 whereas a value of 1 corresponds to the beamlet of the row opening being an open space that is not occupied by metal leaves 212.

Figure 2B:
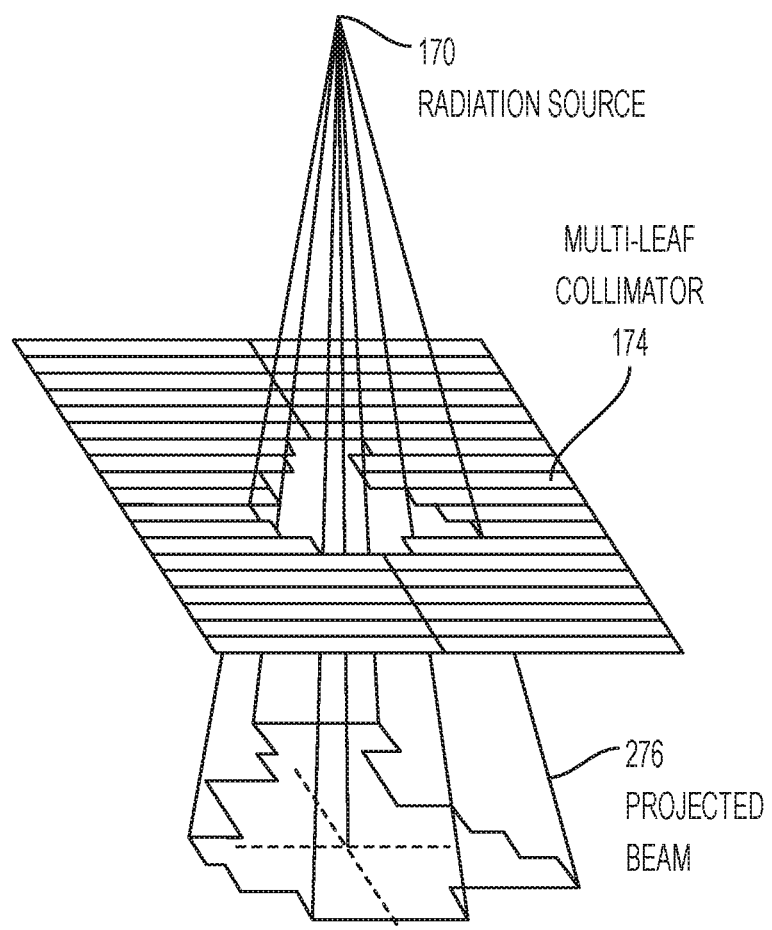
FIG. 2B is a block diagram that illustrates an example of a projected beam from the radiation source that is shaped by the collimator of FIG. 1A, according to an embodiment.

FIG. 2B is an block diagram that illustrates an example of a projected beam 276 from the radiation source 170 that is shaped by the beamlet values of the row openings 210 of the collimator 174 of FIG. 1A, according to an embodiment. Depending on the beamlet values of the row openings 210 within the collimator 174, the radiation beam 172 of FIG. 1A is selectively transmitted or blocked at each area element, resulting in the projected beam 276 taking a specific shape and penetrating particular voxels 122 within the volume 124.

In an embodiment, the values of the row openings 210 are adjusted for each angle 171 such that the radiation beam 172 is selectively shaped at each angle 171 and consequently irradiates the voxels 122 of the volume 124 with a selective shape given by the aperture 211 at each angle 171. For each angle 171 of index i, a set of row openings 210 of index k is represented by $K_i$, where each row opening of index k in the set $K_i$ has one or more open area elements or beamlets. In an example embodiment, if the surface area of the MLC 174 is divided into 100 rows, $K_1$ is a set of row openings at a first angle 171 of index i=1 that may include row openings at row #1, 37 and 59 of the 100 rows of the MLC 174, whereas $K_2$ is a set of row openings at a second angle 171 of index i=2 that may include row openings at row #2, 38, 61 of the 100 rows of the MLC 174. In some IMRT embodiments, multiple apertures are used at each angle, each aperture used with a corresponding constant or variable radiation source intensity. The net effect is a variable intensity beam directed to the subject at each angle. A part of each beam at each angle goes through a single beamlet of the row opening 210, with the net intensity of the several beamlets and radiation source intensities used at that angle.

Figure 3:
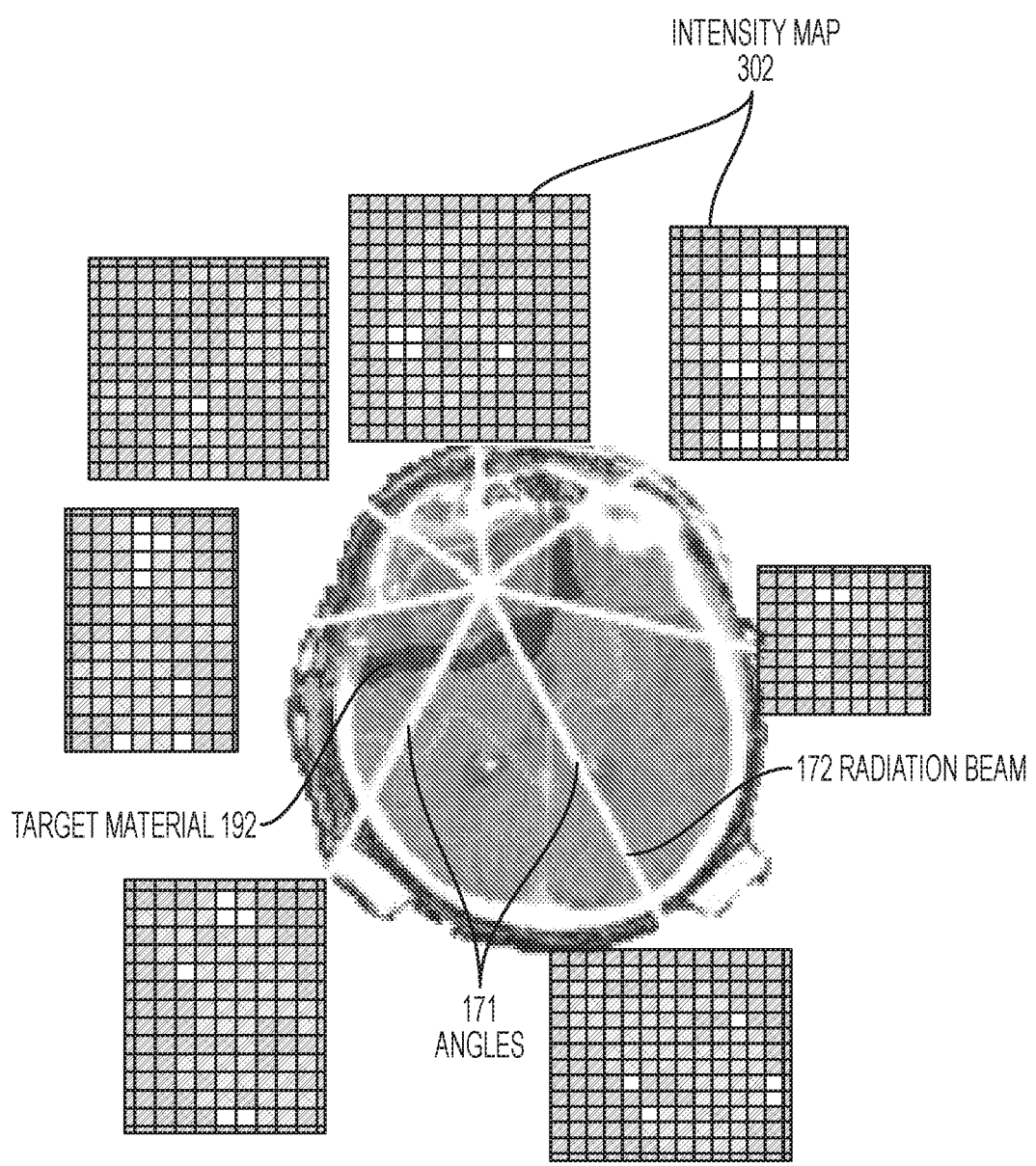
FIG. 3 is an block diagram that illustrates a plurality of intensity maps of the radiation beam of FIG. 1A at a plurality of angles associated with an image of a subject, according to an embodiment.

FIG. 3 is an image that illustrates a plurality of intensity maps 302 of the radiation beam 172 of FIG. 1A at a plurality of (7) angles 171, according to an embodiment. The radiation beam 172 penetrates the target material 192 from the plurality of angles 171. The intensity map 302 displays the intensity and shape of the beam 172 at each angle 171, where each beamlet of each row opening 210 is a shade of gray that indicates a corresponding intensity due to the net effect of multiple row openings 210 and radiation source intensities. The values of the intensity map 302 at each angle 171 are based on a product of the value of each row opening 210 beamlet (FIG. 2A) and an intensity of the beam 172 at each of several row openings 210.

The dose delivered to each voxel can be computed by summing the intensity of the beam impinging on each voxel and accounting for absorption of the beam intensity by other voxels that lie on the beamlet between the source and the current voxel. For a particular plan of operating the radiation source at the various intensities, angles and apertures, the actual dose delivered may deviate from the target dose desired. To optimize a plan, the deviation from the target dose contributes to a penalty and the plan is modified to minimize the penalty. In typical optimization plans, there are one or more penalties computed, each dependent on a different kind of tissue and the radiation plan. The relationship between the penalty and the radiation plan for each tissue type is called the objective function to be minimized. In a previous patent, a method to combine the objective functions for the various tissues is based on a weighted sum of the separate objective functions, where the weighting is based on a target dose range for each tissue type. However, the objective functions for the various tissues can be combined based on any weighting method that is appreciated by one of ordinary skill in the art and need not be based on the target dose range for each tissue type.

Figure 4:
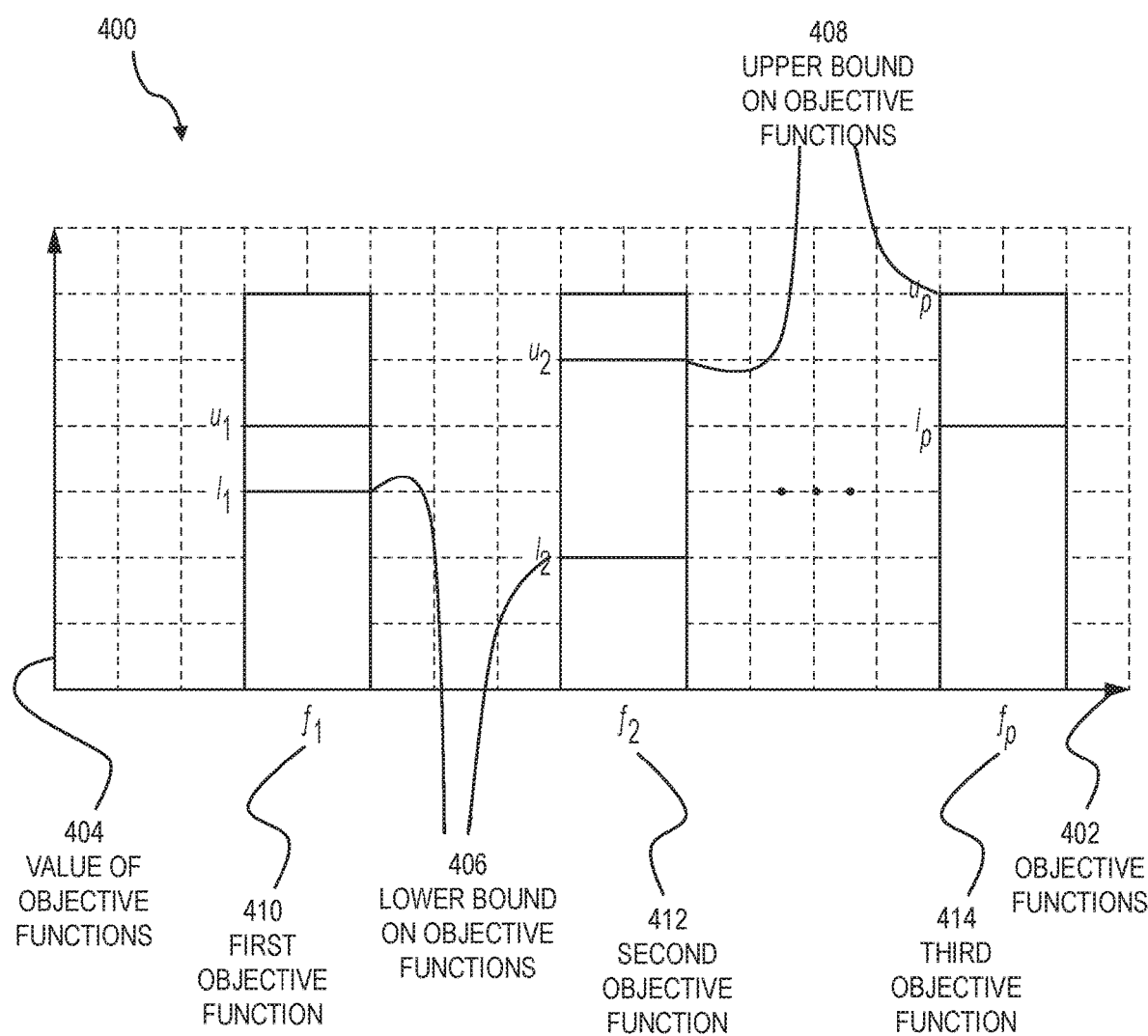
FIG. 4 is a graph that illustrates an example of upper and lower bounds of a plurality of objective functions, according to an embodiment.

FIG. 4 is a graph 400 that illustrates an example of upper and lower bounds of a plurality of objective functions 410, 412, 414, according to an embodiment. These upper and lower bounds are used to scale the various objective functions so that they can be summed to produce a single objective function that can be minimized using standard techniques. In one embodiment, each objective function 410, 412, 414 is associated with a respective tissue type within the subject 190 among the target material 192, the OAR 194 material, the critical organ 195 material and the normal tissue material. In an example embodiment, the first objective function 410 is associated with the target material 192, the second objective function 412 is associated with the OAR 194 material and the third objective function 414 is associated with the critical organ 195 material. Although the graph 400 depicts three objective functions, the system 100 is not limited to three objective functions and can include less or more than three objective functions, where each objective function is associated with a respective tissue type of the subject 190. Such an example is described in more detail below.

As shown in the graph 400 of FIG. 4, the horizontal axis 402 indicates the different objective functions. The vertical axis 404 indicates the value of the objective functions. For each objective function 410, 412, 414, a lower bound 406 is depicted and an upper bound 408 is depicted. In an example embodiment, the lower bounds 406 and the upper bounds 408 for each objective function 410, 412, 414 are provided by a user of the system 100 and manually entered into the computer system 150. Although FIG. 4 depicts the upper and lower bounds 408, 406 of the three objective functions 410, 412, 414, these upper and lower bounds are not shown to scale and thus the upper bound 408 of the third objective function 414 may be less than the upper bounds 408 of the first and second objective functions 410, 412, for example.

In one embodiment, the objective function 410 associated with the target material 192 is a maximum variation between a prescription radiation dose, $PD_t$, to the target material 192 and a radiation dose $z_1$ received at each voxel 122 (with index 1) within the target material 192, expressed as:

$$\max_{l \varepsilon V_t} |z_l - PD_t| \quad (1)$$

where $V_t$ represents the volume within the target material 192.

In one embodiment, the objective function 412 associated with the OAR 194 material is a mean radiation dose within the OAR 194, expressed as:

$$\frac{\sum_{l \varepsilon V_o} z_l}{|V_o|} \quad (2)$$

where $z_1$ is the radiation dose received at each voxel 122 (with index 1) within the OAR 194, $V_o$ represents the volume within the OAR 194 and $|V_o|$ is the number of voxels 122 within the OAR 194.

In one embodiment, the objective function 414 associated with the critical organ 195 material is a maximum dose within the critical organ 195, expressed as:

$$\max_{l \varepsilon Vc} z_l \quad (3)$$

where $z_1$ is the radiation dose received at each voxel 122 (with index 1) within the critical organ 195 and $V_o$ represents the volume of the critical organ 195.

In one embodiment, an objective function associated with the normal tissue material is a maximum dose within the normal tissue, expressed as:

$$\max_{l \varepsilon V n} z_l \quad (4)$$

where $z_1$ is the radiation dose received at each voxel 122 (with index 1) within the normal tissue and $V_n$ represents the volume of the normal tissue.

The radiation dose $z_1$ received at each voxel 122 (index 1), which is used in equations (1)-(4), is a function with intensity was a variable, deposition time D as a known input, and with a predetermined set of angles and apertures as constants. In an embodiment, the radiation dose $z_1$ received at each voxel 122 (index 1) can be expressed as:

$$z_l = \sum_{i \varepsilon \theta} \sum_{k \varepsilon Ki} w_{ik} \left( \sum_{j \varepsilon Ak} D_{ijl} \right) \quad (5)$$

where i is an index of the angle 171; $\theta$ is the plurality of angles 171; k is the index of each row opening 210; K, is the aperture equal to the set of row openings 210 at the $i^{th}$ angle; $w_k$ is the intensity value of the beam 172 at the $k^{th}$ row opening of the $i^{th}$ angle 171; j is an index of the beamlet within the beam 172; $A_k$ is a set of exposed (non-blocked) beamlets in the $k^{th}$ row opening; and $D_{ijl}$ is the dose deposition based on an amount of time that the beamlet of index j impinges the voxel of index 1 at the angle of index i. The values of the row openings 210 are factored in equation (5) by $A_k$, since the values of the row openings 210 affect which beamlets of index j are exposed through each row opening of index k. When optimizing a radiation plan in the presence of continuous gantry motion according to various embodiments of BCAT, $w_{ik}$ in Equation 5 is replaced as explained next.

FIG. 1D is a block diagram that illustrates an example system 100' for optimizing a treatment plan for irradiation therapy, according to an embodiment. The system 100' is similar to the system 100 of FIG. 1A with the exception of the features discussed herein. Although not depicted in FIG. 1D, the system 100' includes the systems volume 124 that defines the voxels 122 that encompass part of the subject. The system 100' includes an imaging system 121' that is similar to the imaging system 121. The system 100' includes a radiation therapy component with radiation source 170, except that the radiation source 170 continuously moves at a gantry speed 180 through an arc including a plurality of therapy angles 171a, 171b, 171c. The gantry speed 180 is a rotational speed and thus the radiation source 170 rotates with an angular rate of change through the arc, based on a magnitude of the gantry speed 180. In some embodiments, the gantry speed 180 is variable through the arc. In an example embodiment, the gantry speed 180 at each therapy angle 171a, 171b, 171c is determined using the method 550 of FIG. 5B. In an example embodiment, a variation of the gantry speed 180 between consecutive therapy angles 171a, 171b is limited by an upper bound. In one example embodiment, the gantry speed 180 between therapy angles 171a, 171b, 171c is set to an upper bound. In other embodiments, the gantry speed 180 is fixed through the arc. In an example embodiment, a magnitude of the gantry speed 180 has an upper bound and a lower bound. In some embodiments, the gantry speed 180 is greater than zero throughout the arc and thus the radiation source 170 does not stop moving through the arc.

FIG. 1E is a block diagram that illustrates an example of an arc of the system of FIG. 1D divided into a plurality of computational angles 171 including therapy angles 171a, 171b etc., and non-therapy angles 171z, according to an embodiment. The radiation source 170 is turned on at each therapy angle 171a, 171b etc., whereas the radiation source 170 is turned off at the non-therapy angles 171z. In some embodiments, the radiation source 170 is turned off at one or more non-therapy angles 171z. Zero or more intervening angles or non-therapy angles 171z are positioned between consecutive therapy angles 171a, 171b, etc. The arc is divided into the plurality of computational angles 171, such that an angular increment 173 is provided between each computational angle 171, including between consecutive non-therapy angles 171z and between a therapy angle 171a and an adjacent non-therapy angle 171z or between two contiguous therapy angles, not shown. In various embodiments, the 360 degrees of angles are broken up into angle increments 173 of between 0.1 and 10 degrees. In an example embodiment, the angular increment 173 between adjacent angles for computation (e.g., for computation of gantry speed, weight $w_i$, among others) is 2 degrees. For purposes of this description, "angle" shall mean computational angle 171 (e.g. therapy angles 171a and non-therapy angles 171z collectively), unless indicated otherwise. In the embodiment of FIG. 1E, the arc is divided into sixty computational angles 171 that include two therapy angles 171a and 171b and multiple non-therapy angles 171z between consecutive therapy angles. However, in other embodiments, the arc is divided into 170 or more computational angles 171 including 10 or fewer therapy angles with zero or more non-therapy angles in between adjacent therapy angles. At each therapy angle, the beam intensity is on for an angular width 175 equal in size to the computational angular increment 173 but centered on the therapy angle.

During operation of the system 100', the radiation source 170 rotates at the gantry speed 180 through the arc including the plurality of therapy angles 171a, 171b, 171c, etc. At each therapy angle, a beam intensity of the radiation source 170 and an aperture 211 of the collimator 174 is selected that determines a specific intensity and shape of the beam 172 that irradiates voxels 122 within the systems volume 124 at that angle. In some embodiments, the beam 172 is turned on over an angular width 175 centered at each therapy angle. In the example embodiment of FIG. 1D, the angular width 175 is equal in size to the angular increment 173. In some embodiments, at the non-therapy angles 171z between consecutive therapy angles 171a, 171b, the radiation source 170 is turned off. In other embodiments, the radiation source 170 is left on at one or more non-therapy angles 171z but at reduced intensity.

In some embodiments, after the radiation source 170 has moved through a first arc including the plurality of therapy angles 171a, 171b, 171c at the gantry speed 180, the radiation source 170 moves through a negative arc including a plurality of therapy angles 171d, 171e at a gantry speed 181 that has an opposite direction to the gantry speed 180 of the first arc. As with the therapy angles 171a, 171b, 171c of the first arc, non-therapy angles 171z are positioned between the therapy angles 171d, 171e of the negative arc. Although the first arc is depicted as encompassing the plurality of therapy angles 171a, 171b, 171c and the negative arc is depicted as encompassing the plurality of therapy angles 171d, 171e, the first and second arc are not limited to this angular range or this number of angles. In other embodiments, the first arc and negative arc share the same angular range and/or the same angles. In still other embodiments, the radiation source 170 can move through multiple arcs in a same direction (e.g. where the gantry speeds 180, 181 are oriented in the same direction).

Unlike the radiation source 170 of the system 100 that stops at each therapy angle 171, in some embodiments the radiation source 170 of the system 100' continuously moves through each therapy angle 171a, 171b, 171c. In other embodiments, the radiation source 170 of the system 100' stops at one or more therapy angle 171a, 171b, 171c, if a required dose at the therapy angle exceeds a threshold dose. Thus, the aperture 211 of the collimator 174 has a limited amount of time to transition from an aperture 211a at the therapy angle 171a to an aperture 211b at the therapy angle 171b. In some embodiments, this limited time is based on a magnitude of the gantry speed 180 between the therapy angles 171a, 171b and an angular spacing 177 between the therapy angles 171a, 171b, which in turn is based on a total time for treatment. It is advantageous or both operator and subject patient for the total treatment time to be a short as possible. In an example embodiment, this limited time is a rotation time based on a ratio of the angular spacing 177 to the magnitude of the gantry speed 180 between the therapy angles 171a, 171b. The embodiment of the optimized radiation control process 140' takes account of the gantry speed and the rate of change of the aperture from 211a to 211b.

In some embodiments, to effectively adjust from the aperture 211a at the therapy angle 171a to the aperture 211b at the therapy angle 171b, the aperture or gantry speed of the plan is constrained so that an adjustment time of the collimator 174 from the aperture 211a to the aperture 211b is less than or equal to the rotation time of the radiation source 170 between the therapy angles 171a, 171b.

Figure 2C:
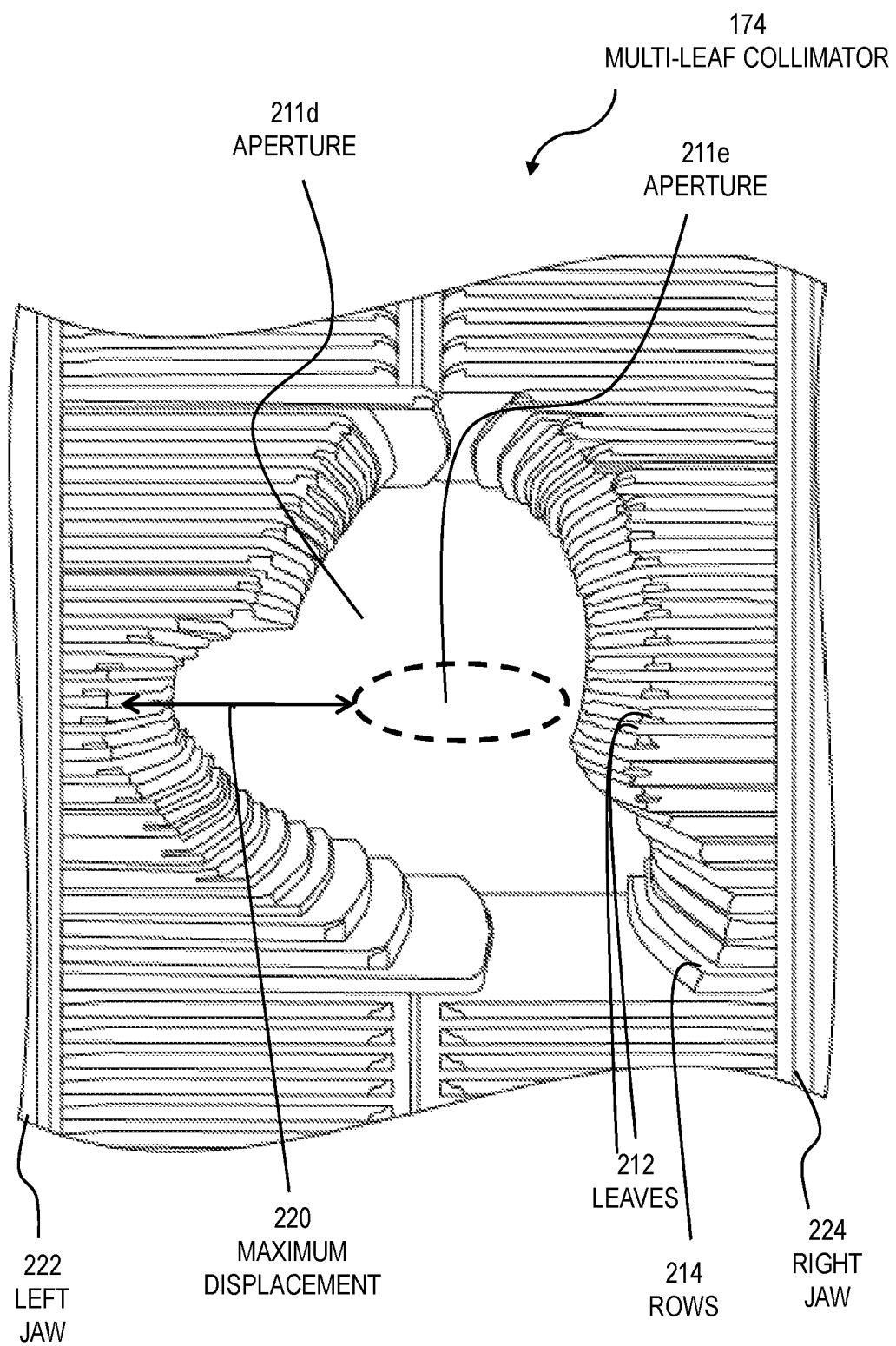
FIG. 2C is an image that illustrates an example of a multi-leaf collimator (MLC) used in the system of FIG. 1D, according to an embodiment.
Figure 2D:
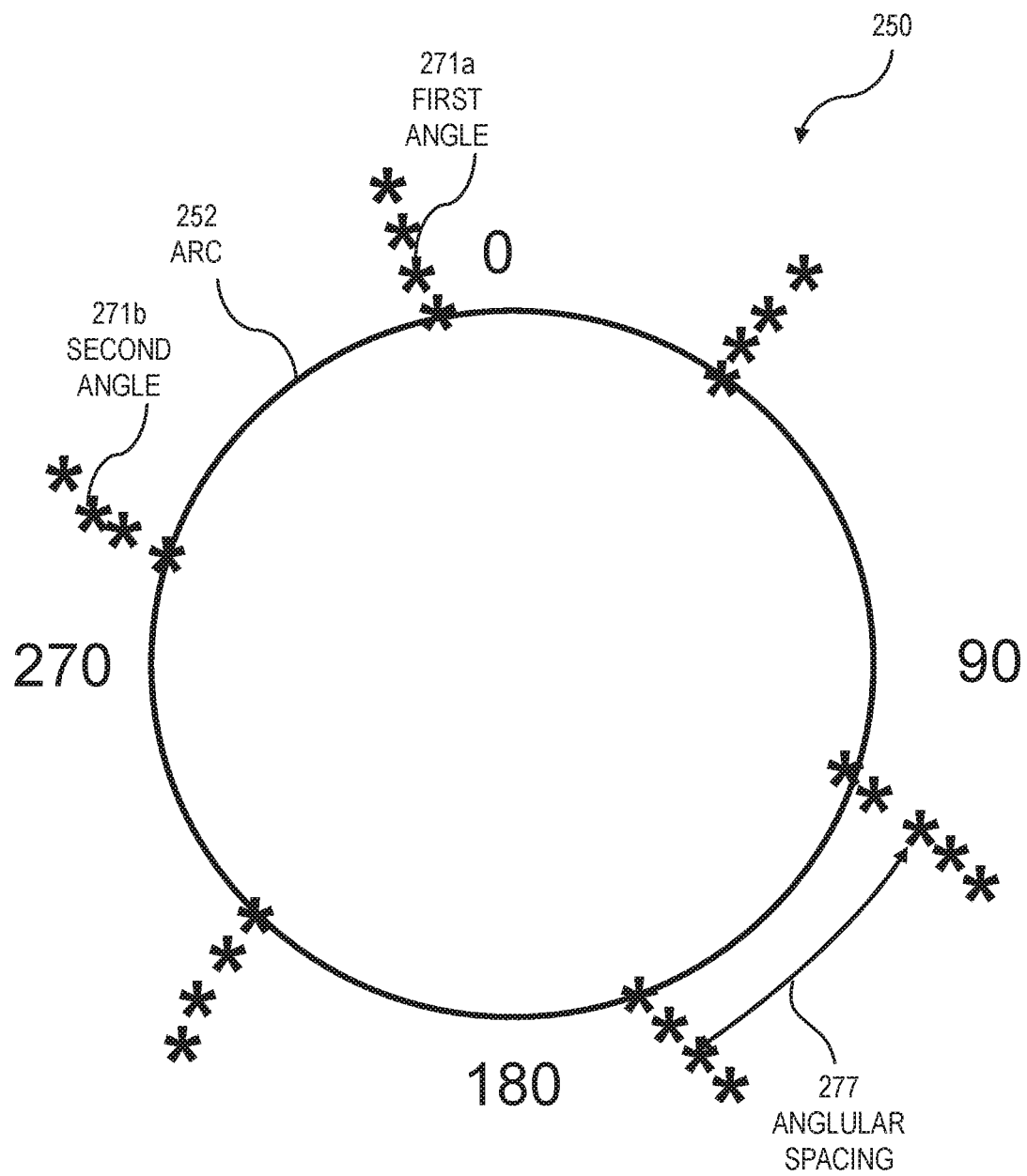
FIG. 2D is a block diagram that illustrates an example of a conventional system for optimizing a treatment plan for irradiation therapy.

FIG. 2C is block diagram that illustrates an example of the multi-leaf collimator (MLC) 174 used in the system 100' of FIG. 1D, according to an embodiment. A surface area of the MLC 174 includes the aperture 211 that represents the plurality of row openings 210. The aperture 211 is formed by selectively moving metal leaves 212 within rows 214. A left column of metal leaves 212 move relative to the left jaw 222 within the rows 214 and a right column of metal leaves 212 move relative to the right jaw 224 within the rows 214 to form the aperture 211. Among all of the metal leaves 212 of the MLC 174, one of the metal leaves 212 requires a maximum displacement 220 to transition from the aperture 211d to the aperture 211e. In some embodiments, the adjustment time of the collimator 174 is based on the maximum displacement 220 and an aperture rate of change or adjustment speed of the metal leaves 212. In an example embodiment, the adjustment time of the collimator 174 is a ratio of the maximum displacement 220 to the adjustment speed. In an example embodiment, the range of maximum adjustment speed of the metal leaves 212 is between 1 centimeter/second (cm/sec) and 2.5 cm/sec.

As illustrated in FIG. 1D, a computer system 150' is provided that is similar to the computer system 150 of the system 100 and is used to control the one or more imaging system 121', to collect imaging data from the one or more imaging system 121', and to determine a treatment plan including aperture values (e.g. beamlet values of the multiple row openings 210 making up the aperture 211) of the collimator 174 and intensity of the radiation source 170 at each therapy angle 171a, 171b, 171c. The computer system 150' includes an optimized radiation control process 140' to perform one or more steps of a method described below with reference to FIG. 5A. In various embodiments, the computer system 150' comprises one or more general purpose computer systems, as depicted in FIG. 7 or one or more chip sets as depicted in FIG. 8, and instructions to cause the computer or chip set to perform one or more steps of a method described below with reference to FIG. 5A.

In some embodiments, the system 100' uses the same objective functions for the various tissue types that are defined by equations (1)-(4) for some embodiments. The radiation dose $z_1$ received at each voxel 122 (index 1), which is used in equations (1)-(4), is a function with weight w that now depends only on angle i, because the row openings also depend on the angle i as a variable, the deposition time D as a known input and with a predetermined set of angles as constants. Thus, in some embodiments, Equation 5 is replaced by Equations 6 and 7; and, the radiation dose $z_1$ received at each voxel 122 (index 1) can be expressed as:

$$z_l = \sum_{i=1}^{\theta} w_i \left( \sum_{j \in A_i} D_{ijl} \right) \quad (6)$$

where i is an index of the computational angles 171; θ is the plurality of computational angles 171; $w_i$ is the weight factor of the beam 172 at the $i^{th}$ computational angle 171; j is an index of the beamlet within the beam 172; $A_i$ is a set of exposed (non-blocked) beamlets at the $i^{th}$ computational angle; and $D_{ijl}$ is the dose deposition based on an amount of time that the beamlet of index j impinges the voxel of index l at the computational angle of index i. In some embodiments, since the beam 172 is off at one or more non-therapy angles 171z, $w_i$ is zero for the indices i corresponding to these non-therapy angles 171z. In some embodiments, $w_i$ is zero for the indices i corresponding to all non-therapy angles 171z. The values of the aperture 211 is factored in equation (6) by $A_i$, since the values of the aperture 211 affects which beamlets of index j are exposed through each angle of index i. In some embodiments, the weight $w_i$ at each therapy angle can be expressed as:

$$w_i = \frac{\omega_i \delta_i}{v_i} \qquad (7)$$

where $\omega_i$ is intensity of the beam 172 (in units of monitor units per second, MU/sec); $\delta_i$ is the angular increment 173 between the i and i+1 computational angle for which the beam is continuously on and $v_i$ is the angular rate of change of the radiation source 170 at the $i^{th}$ computational angle 171 based on the gantry speed 180. In some embodiments, the gantry speed or angular rate of change $v_i$ at each therapy angle is determined using the method 500 of FIG. 5B. As depicted in FIG. 1D, $\delta_i$ is the therapy angular width 175 centered on the therapy angle 171a for which the beam is continuously on. By substituting equation (7) into equation (6), the radiation dose $z_l$ can be expressed as:

$$z_l = \sum_{i=1}^{\theta} \frac{\omega_i \delta_i}{v_i} \left( \sum_{j \in A_i} D_{ijl} \right) \qquad (8)$$

Figure 5A:
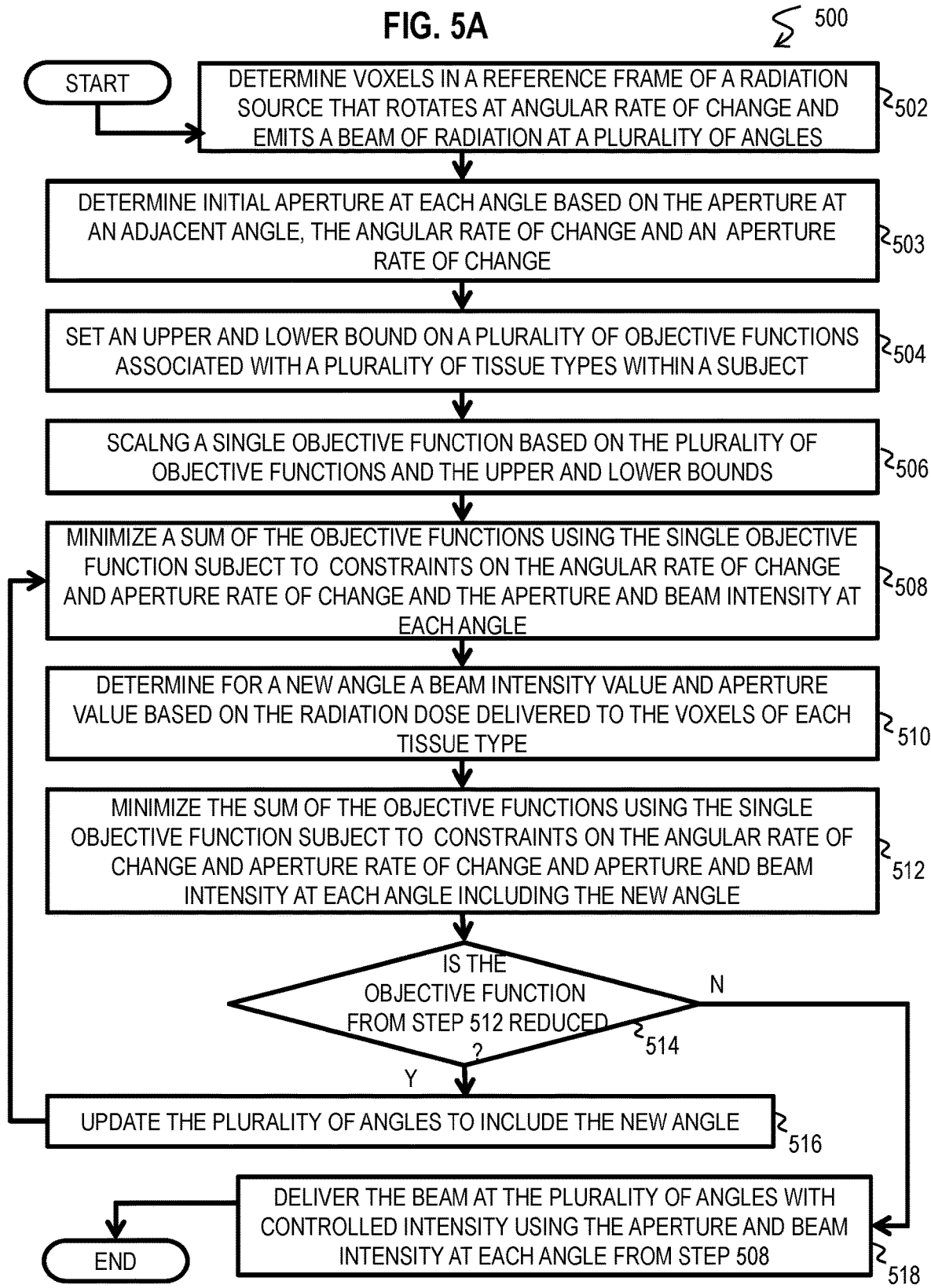
FIG. 5A is a flow diagram that illustrates an example of a method for optimizing a treatment plan for irradiation therapy, according to an embodiment.

FIG. 5A is a flow diagram that illustrates an example of a method 500 for optimizing a treatment plan for irradiation therapy, according to an embodiment. This embodiment achieves a solution that is constrained by the maximum rate of change of an aperture of the collimator or the limits on the rate of change of gantry speed or the limits on the rate of change of intensity $\omega_i$ or some combination and includes options to turn the beam off at some non-therapy angles between therapy angles. For example, one or more of the steps of method 500 are applied by process 140' of computer system 150'. Although the flow diagram of FIG. 5A is depicted as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

After starting, in step 502, the voxels 122 are defined for the subject 190 in the fixed reference frame for the radiation source 170 for which the radiation beam 172 shape and intensity can be controlled by aperture values of the collimator 174 at each therapy angle 171a. As depicted in FIG. 1C, the voxels 122 are defined by the three-dimensional axes 102, 104, 106 in the fixed reference frame of the radiation source 170. Additionally, the voxels 122 are positioned within the systems volume 124 that encompasses a portion of the subject 190, such that each voxel 122 is a respective volume element within the volume 124. Additionally, as previously discussed, the intensity and shape of the beam 172 at each therapy angle 171a can be controlled by the computer system 150' adjusting one or more values of the one or more row openings 210 of the collimator 174 at each therapy angle 171a or gantry speed or whether the radiation source is on or off, or some combination.

In step 503, an initial aperture 211 is determined at each angle 171a, 171b, 171c in the first arc. In some embodiments, the initial aperture 211 at each angle 171a, 171b, 171c is based on an aperture 211 at an adjacent angle, the angular rate of change of the radiation source 170 based on one or more values of gantry speed 180 in the range of allowed gantry speeds and the aperture rate of change of the collimator 174. In these embodiments, the initial aperture 211b at the angle 171b is based on the aperture 211a at the adjacent angle 171a, the gantry speed 180 between the angle 171b and the adjacent angle 171a, and the adjustment speed of the metal leaves 212 within the collimator 174. In some embodiments, the initial aperture 211 at each therapy angle 171a, 171b, 171c is based on an aperture 211 at an adjacent therapy angle 171a, 171b, 171c. In other embodiments, the initial aperture 211 at each therapy angle 171a, 171b, 171c is based on an aperture 211 at an adjacent non-therapy angle 171z to the therapy angle. Although the beam 172 is not turned on at the non-therapy angles 171z, the aperture 211 of the collimator 174 adjusts at the non-therapy angles 171z between consecutive therapy angles 171a, 171b.

In some embodiments, in step 503, a rotation time is determined of the radiation source 170 from the adjacent angle 171a to the angle 171b, based on a ratio of the angular spacing 177 between the adjacent angle 171a and the angle 171b and the selected value or values of the gantry speed 180 between the adjacent angle 171a and the angle 171b. In some embodiments, the values of the gantry speed 180 at each angle 171 are determined using the method 550 of FIG. 5B. In other embodiments, the rotation time is determined from the therapy angle 171b to an adjacent non-therapy angle 171z based a ratio of the angular increment 173 between the therapy angle 171b and adjacent non-therapy angle 171z and the selective value of the gantry speed 180 between the therapy angle 171b and adjacent non-therapy angle 171z.

Additionally, in step 503, an adjustment time of the collimator 174 is determined from the aperture 211a at the adjacent angle 171a to the initial aperture 211b at the angle 171b based on a ratio of the maximum displacement 220 of the metal leaves 212 between the apertures 211a, 211b and the adjustment speed of the metal leaves 212 within the collimator 174. In other embodiments, the adjustment time of the collimator 174 is determined from an aperture 211 at an adjacent non-therapy angle 171z to the initial aperture 211b at the therapy angle 171b based on a ratio of the maximum displacement 220 of the metal leaves 212 between the aperture 211 at the adjacent non-therapy angle 171z and the initial aperture 211b and the adjustment speed of the metal leaves 212.

In some embodiments, the initial aperture 211b at the angle 171b is selected such that the adjustment time is less than or equal to the rotation time. Consequently, the initial aperture 211 at each angle 171 is selected within a limited range that is based on the initial aperture at the adjacent angle, the gantry speed 180 and the adjustment speed of the collimator 174. In some embodiments, the initial aperture 211 at each therapy angle 171 is selected based on an initial aperture at an adjacent non-therapy angle 171z, the gantry speed 180 and the adjustment speed of the collimator 174. In some embodiments, gantry speed is adjusted to allow sufficient time to change the aperture as desired or close to a desired aperture, taking into account gantry speed at the previous angle (e.g., the adjacent non-therapy angle 171z to the therapy angle 171) and the rate of change of gantry speed. In some of these embodiments, the gantry speed is greater than zero at all angles including all therapy angles 171 and non-therapy angles 171z. Step 503 is repeated for each therapy angle 171a, 171b, 171c in the arc. In other embodiments, step 503 is repeated for each computational angle 171 including non-therapy angles 171z.

In some embodiments, in step 503, a user is prompted to input a desired treatment time. In an example embodiment, the user is prompted to input a desired maximum treatment time. Based on the inputted desired treatment time, a minimum gantry speed is determined, in order to complete the treatment within the desired treatment time. The determination of the minimum gantry speed is based on the inputted desired treatment time, the number of required arcs for the treatment and the total angular range of the number of arcs for the treatment. In some embodiments, the range of allowed gantry speeds 180, including a lower bound on the gantry speed 180, is adjusted based on the determined minimum gantry speed. In an example embodiment, the lower bound on the gantry speed 180 is set to the determined minimum gantry speed. In this embodiment, during step 503, the initial apertures 211 at each therapy angle 171a are determined, based on this adjusted range of allowed gantry speeds 180. In other embodiments, if the determined minimum gantry speed is above an upper bound of the gantry speed 180, the user is notified that the treatment cannot be performed within the inputted desired treatment time and is prompted to re-enter another desired treatment time.

In other embodiments, where the radiation source 170 is moved through the plurality of therapy angles 171a, 171b, 171c of the first arc at gantry speed 180 and through the plurality of therapy angles 171d, 171e of the second arc at gantry speed 181, step 503 is also performed for each of the angles 171d, 171e of the second arc. In these embodiments, the gantry speed 181 is used to determine the initial apertures 211 at each of the therapy angles 171d, 171e in a similar manner as the gantry speed 180 was used to determine the initial apertures 211 during the first arc. In an example embodiment, the second arc includes one or more therapy angles 171a, 171b, 171c of the first arc, where the radiation source 170 moves in an opposite direction (e.g., gantry speed 181) than during the first arc (e.g., gantry speed 180).

In some embodiments, during step 503, an initial beam intensity is determined at each therapy angle 171a, 171b, 171c in the first arc. In some embodiments, the initial beam intensity at the therapy angle 171b is based on the initial beam intensity value at the adjacent therapy angle 171a, a maximum variation of the beam intensity from the adjacent therapy angle 171a to the therapy angle 171b, a lower bound of the beam intensity and an upper bound of the beam intensity. In other embodiments, where the radiation source 170 is moved through the plurality of therapy angles 171d, 171e of the second arc at gantry speed 181, step 503 is also performed to determine an initial beam intensity at each therapy angle 171d, 171e in the second arc. In one embodiment, the initial beam intensity value at each therapy angle 171 is selected, such that the intensity of the projected beam 276 (FIG. 2B) corresponds to the prescription radiation dose $PD_t$ delivered to the target material 192 at each therapy angle 171.

In step 504, the upper bounds 408 and lower bounds 406 are set for each objective function 410, 412, 414 that is associated with a respective tissue type within the subject 190. In one embodiment, the upper bounds 408 and lower bounds 406 of the objective functions 410, 412, 414 are manually input to the computer system 150' by a user. In an example embodiment, where the first objective function 410 is associated with the target material 192 and expressed as equation (1), in step 504 the upper bound 408 and lower bound 406 for the value of equation (1) are set. In an example embodiment, where the second objective function 412 is associated with the OAR 194 material and expressed as equation (2), in step 504 the upper bound 408 and lower bound 406 for the value of equation (2) are set. In an example embodiment, where the third objective function 414 is associated with the critical organ 195 material and expressed as equation (3), in step 504 the upper bound 408 and lower bound 406 for the value of equation (3) are set. In an example embodiment, where the fourth objective function is associated with the normal tissue material and expressed as equation (4), in step 504 the upper bound 408 and lower bound 406 for the value of equation (4) are set. In other embodiments, each objective function 410, 412, 414 is scaled using any weighting method that is appreciated by one of ordinary skill in the art. In these embodiments, step 504 is omitted.

In step 506, parameters are defined for each objective function 410, 412, 414. In some embodiments, the parameters are defined, based on the upper bounds 408 and lower bounds 406 for the objective functions 410, 412, 414 that were set in step 504. The parameters are used to scale the separate objective functions so that they can be summed into a single objective function and attributed the correct relative weights. The single objective function can then be minimized using any standard techniques known in the art. In one embodiment, a first parameter for each objective function 410, 412, 414 is the upper bound 408 of the objective function. In another embodiment, a second parameter is a reciprocal of a difference between the upper bound 408 and lower bound 406 of the objective function. However, the parameters are not limited to these specific parameters and can include any parameters that are based on the upper bound 408 and/or the lower bound 406 of each objective function. In other embodiments, the parameters can be defined using any weighting method that is appreciated by one of ordinary skill in the art.

In step 508, the single objective function, a sum of the properly scaled objective functions 410, 412, 414 from step 506, is minimized, subject to one or more constraints. In some embodiments, the constraint is on the aperture rate of change, expressed as:

$$g_t(A_i, A_{i+1}) \leq \frac{\delta_i}{v_i} \quad i = 1, \ldots \theta \tag{9}$$

where $g_t(A_i, A_{i+1})$ is an adjustment time of the collimator 174 from the aperture at the computational angle 171 of index i to the aperture at the computational angle 171 of index i+1 and where $\delta_i/v_i$ is a rotation time of the radiation source 170 from the computational angle of index i to the computational angle of index i+1, expressed as a ratio of the angular increment 173 ($\delta_i$) between the computational angles to an angular rate of change ($v_i$) between the computational angles. Note that the index i is an index of the computational angles and thus is not confined to the therapy angles but includes every computational angle including every therapy and non-therapy angle in the arc, e.g., every 2 degrees from 0 to 360, so i goes from 0 to 180. The adjustment time $g_i$ is related to the adjustment speed of the collimator by:

$$g_t(A_i, A_{i'}) \cdot \frac{\max_{h \in (1,\ldots m)} \max(|l_{hi} - l'_{hi}|, |r_{hi} - r_{hi'}|)}{v} \quad (10)$$

where h is an index of rows 214 of metal leaves 212 in the MLC 174; m is the number of rows of index h in the MLC 174; $l_{hi}$ is an extension length of the left metal leaves 212 from the left jaw 222 in the row of index h at the angle of index i; $l_{hi'}$ is an extension length of the left metal leaves 212 from the left jaw 222 in the row of index h at the angle of index i'; $r_{hi}$ is an extension length of the right metal leaves 212 from the right jaw 224 in the row of index h at the angle of index i; $r_{hi'}$ is an extension length of the right metal leaves 212 from the right jaw 224 in the row of index h at the angle of index i'; v is the adjustment speed of the metal leaves 212. The numerator of equation (10) is the maximum displacement 220 among all of the leaves 212 during the transition from the aperture at the angle of index i to the aperture at the angle of index i'. Equations (9) and (10) require that the adjustment speed of the metal leaves 212 is at least a minimum speed, such that the adjustment time of the collimator 174 (left side of equation 9) is less than or equal to the rotation time of the radiation source 170 (right side of equation 9).

In some embodiments, the constraint is on the angular rate of change, expressed as:

$$v_L \leq v_i \leq v_U \, i=1,\ldots \theta \quad (11)$$

where $v_L$ is a lower bound on the angular rate of change and $v_U$ is an upper bound on the angular rate of change for each computational angle of index i. In some embodiments, the lower bound $v_L$ is adjusted based on the inputted desired treatment time by the user in step 503. In other embodiments, the constraint is on a variation of the angular rate of change between consecutive computational angles, expressed as:

$$|v_i - v_{i+1}| \leq \Delta v \, i=1,\ldots \theta \quad (12)$$

where $v_i$ is the angular rate of change at a computational angle of index i, $v_{i+1}$ is the angular rate of change at a computational angle of index i+1 and $\Delta v$ is the maximum variation of the angular rate of change between consecutive computational angles, e.g. between consecutive non-therapy angles 171z or between a therapy angle 171a and an adjacent non-therapy angle 171z.

In some embodiments, the constraint is on the beam intensity at each angle, expressed as:

$$W^L y_i \leq \omega_i \leq W^U y_i \, i=1,\ldots \theta \quad (13)$$

$$y_i \in \{0,1\} \, i=1,\ldots \theta \quad (14)$$

where $W^L$ is a lower bound on the beam intensity; $W^U$ is an upper bound on the beam intensity and $y_i$ is a binary selection variable that determines whether the beam 172 is on or off at each angle of index i. This constraint ensures that if the beam is on for a therapy angle of index i ($y_i=1$), then the beam intensity $\omega_i$ is within the upper and lower bounds, and the beam intensity is zero for all non-therapy angles. In some embodiments, the beam intensity is on for one or more non-therapy angles. In other embodiments, the constraint is on a variation of the beam intensity between consecutive computational angles, expressed as:

$$|\omega_i - f_{i+1}| \leq \Delta \omega \, i=1,\ldots \theta \quad (15)$$

where $\omega_i$ is the beam intensity at a computational angle of index i, $\omega_{i+1}$ is the beam intensity at a computational angle of index i+1 and $\Delta \omega$ is the maximum variation of the beam intensity between the consecutive computational angles.

In some embodiments, the constraint is that the beam intensity and the angular rate of change at each computational angle is greater than or equal to zero, expressed as:

$$\omega_i \geq 0 \, i=1,\ldots \theta \quad (16)$$

$$v_i \geq 0 \, i=1,\ldots \theta \quad (17)$$

In some embodiments, the beam intensity is zero for all non-therapy angles. In other embodiments, the beam intensity is non-zero for one or more non-therapy angles. In an example embodiment, the beam intensity may be non-zero at an adjacent non-therapy angle to a therapy angle, so that the beam intensity can be adjusted to a desired beam intensity at the therapy angle and conform with the constraint of equation (15).

In some embodiments, the constraint is that a minimum percentage of the target material 192 receives the prescription dose $PD_t$, expressed as:

$$\zeta_s - \frac{1}{(1-\alpha_s)|V_t|} \sum_{l \in V_t} \max(\zeta_s - z_l, 0) \geq PD_t \quad (18)$$

where ξs is a free variable; $\alpha_s$ is the minimum percentage of the target material 192 that receives the prescription dose $PD_t$, $V_t$ is the volume of the target material 192; $z_1$ is the dose received at the voxel of index 1 and $|V_t|$ is the number of voxels within the target material 192.

Proper scaling of the objective functions is achieved using the parameters set in step 506. The single objective function includes initial values for the collective aperture 211 and beam intensity at each angle 171 determined in step 503. In one embodiment, the single objective function is expressed as:

$$\min_{x \in X} \left\{ \max_{j=1,\ldots p} w_j(f_j(x) - r_j) + \rho \sum_{j=1}^{p} w_j(f_j(x) - r_j) \right\} \quad (19)$$

where f is one of the several objective functions having a j index from 1 to p; $r_j$ is the first parameter set in step 506 for the objective function with j index; $w_j$ is the second parameter set in step 506 for the objective function with j index; and p is a small positive number such as 0.0001. In other embodiments, the objective functions 410, 412, 414 are scaled to form a single objective function, using any weighting method that is appreciated by one of ordinary skill in the art.

In one embodiment, the radiation dose $z_1$, expressed in equation (8), is substituted into each of the objective functions expressed in equations (1)-(4). As previously discussed, the value of the aperture 211 is factored in equation (8) by $A_i$, since the exposed beamlets of index j at each computational angle of index i are based on the value of the aperture 211 at each angle 171. Additionally, as previously discussed, equation (8) includes the intensity values $\omega_i$ for the beam 172 for each angle 171. In one embodiment, initial values of the aperture 211 and initial intensity values $\omega_i$ are determined in step 503 for each angle 171, such that each objective function expressed in equations (1)-(4) incorporates the initial values of the aperture 211 and initial intensity values $\omega_i$ at each angle 171. The minimization of equation (19) is subject to the constraints of equations (9)-(18) and results in a beam intensity and aperture 211 at each computational angle 171 and a minimum value of each objective function 410, 412, 414 based on the beam intensity and aperture 211 values, as well as a resulting parameter m associated with each voxel 122 of index 1. Even though the beam intensity is zero at the non-therapy angles 171z, the minimization of equation (19) provides the aperture 211 at each non-therapy angle 171z, in order to establish movement of the aperture 211 of the collimator 174 over the non-therapy angles 171z between consecutive therapy angles 171. In some embodiments, the minimization of equation (19) is performed subject to the constraint of equation (9) and/or equation (11).

In some embodiments, step 508 is simplified by using a fixed angular rate of change $v_i$ at each angle. Additionally, step 508 is simplified by only considering a specific set of therapy angles C where $y_c=1$ and where $y_i=0$ for all other non-therapy angles. Consequently, the minimization of the equation (19) in step 508 is only subject to the constraints of equations (9)-(10), (13), (15), (16) and (18).

In step 510, a new angle is added to the plurality of angles, based on the parameter $\pi_l$. In some embodiments, the new angle is determined with index i, based on:

$$\max_{i \notin C}\left(\max_{\substack{x \in A \\ A \in Ai}} \sum_{j \in Bi}\left(\sum_{l \in V_s} D_{ijl}\pi_l\right)x_i\right) \quad (20)$$

where $x_i$ is a decision variable $\{0,1\}$ based on whether the beamlet of index $j \in B_i$ at angle i is exposed or not. $A_i$ is a set of feasible apertures for the new angle, where the constraint based on equation (9) above is satisfied (e.g. the adjustment time of the collimator 174 from the new angle aperture to the adjacent angle apertures is less than or equal to the rotation time).

If a new angle 171d is added to the plurality of angles 171a, 171b, 171c, then $\theta$ in equation (8) is changed to incorporate this new angle 171d. Additionally, $A_i$ is changed in equation (8) to incorporate the aperture 211 value at the new angle. For example, if the dose at a particular voxel is too high and the dose at a different voxel is too low, then a new angle 171d is added with a new aperture 211 that is open for the beamlets that impinge on the voxel that is too low but is closed for beamlets that impinge on a voxel that is too high. In some embodiments, the initial aperture 211 and initial beam intensity at the new angle 171d is determined in a similar manner as in step 503. In an example embodiment, in step 510, a new therapy angle is added to the plurality of therapy angles 171a, 171b, 171c of the first arc or the plurality of therapy angles 171d, 171e of the second arc. In this example embodiment, the new therapy angle can be added to the therapy angles of the first arc or to the angles of the second arc.

In step 512, the single objective function, the sum of the properly scaled objective functions 410, 412, 414 is minimized and subject to one or more of the constraints of equations (9)-(18). The proper scaling is achieved, using the parameters set in step 506. The single objective function includes the beam intensity and aperture 211 values of the plurality of angles 171a, 171b, 171c and the new angle 171d from step 510. In an embodiment, the minimization of the sum of the objective functions 410, 412, 414 is performed using equation (19), subject to one or more of the constraints of equations (9)-(18), which results in a beam intensity and aperture 211 at each angle and a minimum value for the sum of each objective function 410, 412, 414 based on the beam intensity and aperture 211 values.

In step 514, the value of the single objective function from the minimizing of step 512 is compared with the value of the single objective function from the previous minimizing (e.g., at step 508 the first time through this loop). A determination is made whether the value of the single objective function from the minimizing of step 512 is reduced from the value of the single objective function from the previous minimizing FIG. 6A is a graph 600 that illustrates an example of multiple solutions to the minimizing of a single objective function based on two objective functions $f_1$, $f_2$, according to an embodiment. The horizontal axis 602 is a value of a first objective function $f_1$. The vertical axis 604 is a value of a second objective function $f_2$. The graph 600 shows a shaded region 608 that encompasses solutions to the minimizing of steps 508 and 512, where two objective functions $f_1$, $f_2$ are used. The circled numbers in the shaded region 608 correspond to computed minimum values of $f_1$ and $f_2$ according to the minimizing step. In an example embodiment, the previous minimizing of results in solution #9 and the minimizing of step 512 results in solution #2. In this example embodiment, the value of each objective function $f_1$, $f_2$ from the minimizing of step 512 (2 and 6, respectively) is reduced from the respective value of each objective function $f_1$, $f_2$ from the previous minimizing (6 and 7, respectively). From equation (6), the value of the single objective function is based on values of the objective functions $f_1$ and $f_2$ and thus, the value of the single objective function from the minimizing of step 512 is reduced from the value of the single objective function from the minimizing of step 508.

In step 516, if the determination in step 514 is affirmative, the plurality of therapy angles 171a, 171b, 171c are updated to include the new therapy angle 171d from step 510. As previously discussed, this step involves updating $\theta$ in equation (8) to incorporate the new angle 171d. Additionally, $A_i$ in equation (8) is changed, to incorporate the new angle 171d from step 510. Additionally, $\omega_i$ is changed to incorporate a beam intensity value at the new angle and $\delta_i$ is changed to update angular increments between the angles including the new angle. The method 500 then proceeds to step 508 and uses these updated therapy angles 171a, 171b, 171c, 171d. The method 500 proceeds back to step 508, to perform another iteration of steps 508-514 to ensure that these updated angles in step 516 achieve an optimal or nondominated solution. As shown in FIG. 6A, the shaded region 608 encompassing all solutions to equation (1) includes a pareto front 612 on which the optimal solutions or nondominated solutions 606 reside (solutions #1-6). These nondominated solutions 606 are considered optimal since no reduction in the value of the single objective function is possible, since no reduction in the value of an objective function $f_1$, $f_2$ is possible without increasing the value of the other objective function $f_1$, $f_2$. For example, moving from nondominated solution #2 to solution #12 involves a reduction in the value of $f_2$, but an increase in the value of $f_1$ and thus does not involve a reduction in the value of the single objective function. In another example, moving from nondominated solution #3 to solution #8 involves a reduction in the value of $f_1$ but an increase in the value of $f_2$ and thus similarly does not involves a reduction in the value of the single objective function.

In step 518, if the determination in step 514 is negative, then the value of the single objective function from the minimizing of step 512 has increased from the value of the single objective function from the minimizing of step 508. As a result, the values of the beam intensity and aperture 211 at each angle and resulting values of the objective functions from the minimizing of step 508 is an optimal or nondominated solution 606. In step 518, the beam 172 is delivered at the plurality of therapy angles in step 508 and using the beam intensity and aperture 211 values at each therapy angle determined in step 508. In some embodiments, the beam 172 is turned off at non-therapy angles between the plurality of therapy angles in step 508. In an example embodiment, as shown in FIG. 1D, the beam 172 is turned on over the therapy angular width 175 centered on each therapy angle 171. In another example embodiment, the gantry speed 180 is varied at one or more of the plurality of therapy angles 171 to controllably vary a dose delivered to the voxels at each therapy angle. In an example embodiment, the gantry speed 180 is reduced at one or more of the therapy angles 171 to increase a dose delivered to the voxels at that angle 171. In an example embodiment, the gantry speed 180 is reduced to zero at one or more of the therapy angles 171 where a required dose at those angles 171 exceeds a dose threshold.

In some embodiments, the gantry speed or angular rate of change $v_i$ is determined at each computational angle 171 of index i. FIG. 5B is a flow diagram that illustrates an example of a method 550 for determining the gantry speed 180 at each therapy angle 171a in a treatment plan for irradiation therapy, according to an embodiment. In step 551, a minimum rotation time is determined of the radiation source 170 (e.g. while the beam 172 is on) at the therapy angle 171a. In some embodiments, the beam 172 is on over the therapy angular width 175 centered on the therapy angle 171 (FIG. 1D). The maximum gantry speed or upper bound on the angular rate of change is $v_U$. In these embodiments, the minimum rotation time of the radiation source 170 at the therapy angle 171 is a ratio of the therapy angular width 175 to the maximum gantry speed $v_U$.

In step 553, a minimum dosage time is determined for the beam 172 to deliver a required dosage at the therapy angle 171. In some embodiments, the minimum dosage time is a ratio of the required dosage at the therapy angle 171 to the maximum beam intensity $W^U$.

In step 555, the minimum dosage time from step 553 is compared with the minimum rotation time from step 551. If the minimum dosage time is greater than the minimum rotation time, the method 550 proceeds to step 557. If the minimum dosage time is less than or equal to the minimum rotation time, the method 550 proceeds to step 559.

In step 557, the gantry speed at the therapy angle 171 is adjusted to a value based on a ratio of the therapy angular width 175 to the minimum dosage time from step 553. Since the minimum dosage time from step 553 is greater than the minimum rotation time from step 551, the gantry speed is reduced from the maximum gantry speed $v_U$ to a gantry speed that ensures the beam 172 can deliver the required dose at the therapy angle 171.

In step 559, the gantry speed at the therapy angle 171 is set to the maximum gantry speed $v_U$. Since the minimum dosage time from step 553 is less than or equal to the minimum rotation time from step 551, the beam 172 can deliver the required dosage at the therapy angle 171 while the radiation source 170 moves at the maximum gantry speed $v_U$.

In step 561, if the gantry speed has been determined for all therapy angles 171 in the arc, the method ends. Otherwise, if the gantry speed has not been determined for one or more therapy angles 171, the method 550 proceeds back to step 551.

In some embodiments, the gantry speed at the non-therapy angles 171z is set to the maximum gantry speed $v_U$. During step 518, the gantry speed at each computational angle 171 is adjusted based on the gantry speeds at therapy angles 171 determined in the method 550 and the maximum gantry speed at each non-therapy angle 171z. In other embodiments, the gantry speed at one or more non-therapy angles 171z is set to be less than the maximum gantry speed. In an example embodiment, the gantry speed at a non-therapy angle 171z adjacent to the therapy angle 171 is set to be less than the maximum gantry speed, so that a transition of the gantry speed from the adjacent non-therapy angle 171z to the therapy angle 171 conforms with the constraint of equation (12).

In step 518, the beam 172 is only delivered for a portion of the computational angles which are therapy angles. As discussed in the constraints of equation (13)-(14), the beam intensity is only within the upper and lower bounds for some of the computational angles of index i (e.g. a set C of therapy angles of index i) and the beam intensity is zero at the other non-therapy angles. In an example embodiment, the arc is divided up into over 180 angles of index i and the beam is only delivered for therapy angles that make up only a fraction of those angles, such as 10 to 100 therapy angles or fewer, for example.

In an example embodiment, during a first iteration of steps 508-514, the values of the objective functions move from solution #10 (minimizing step 508) to solution #12 (minimizing step 512) in FIG. 6A. During step 514, since the value of the single objective function was reduced from solution #10 to solution #12, the method proceeds to step 516 and another iteration of steps 508-514 is performed. In this example embodiment, during the second iteration of steps 508-514, the values of the objective functions move from solution #12 (minimizing step 508) to solution #3 (minimizing step 512) in FIG. 6A. Again, during step 514, since the value of the single objective function was reduced from solution #12 to solution #3, the method proceeds to step 516 and another iteration of steps 508-514 is performed. In this example embodiment, during a third iteration of steps 508-514, the values of the objective functions move from solution #3 (minimizing step 508) to a solution (#8, #13, etc) where a value of at least one objective function $f_1$, $f_2$ necessarily increases. During step 514, since the value of the single objective function was not reduced, the solution #3 (from minimizing step 508) is a nondominated solution 606 and thus the method proceeds to step 518 where the values of the row openings 210 of the collimator 174 are adjusted at each angle 171 based on the values of the row openings 210 used in step 508.

2. EXAMPLE EMBODIMENTS

In some embodiments, step 503 is performed to determine an initial aperture 211 at a plurality of angles of an arc. In an example embodiment, the arc includes between 150-200 computational angles, such as 177 angles. In this example embodiment, the initial aperture 211 is determined for between 1-177 therapy angles, such as 5 therapy angles in the arc. In some embodiments, step 503 is performed based on a gantry speed selected within a range between a lower bound of 0.83 degrees/second (deg/sec) and an upper bound of 6 deg/sec. In other embodiments, step 503 is performed based on a fixed gantry speed of 4 deg/sec throughout the arc. In still other embodiments, step 503 is performed based on an adjustment speed of the metal leaves 212 of the collimator 174. In an example embodiment, the adjustment speed is within a range between 2 centimeters/second (cm/sec) and 3 cm/sec, such as 2.25 cm/sec.

Figure 6B:
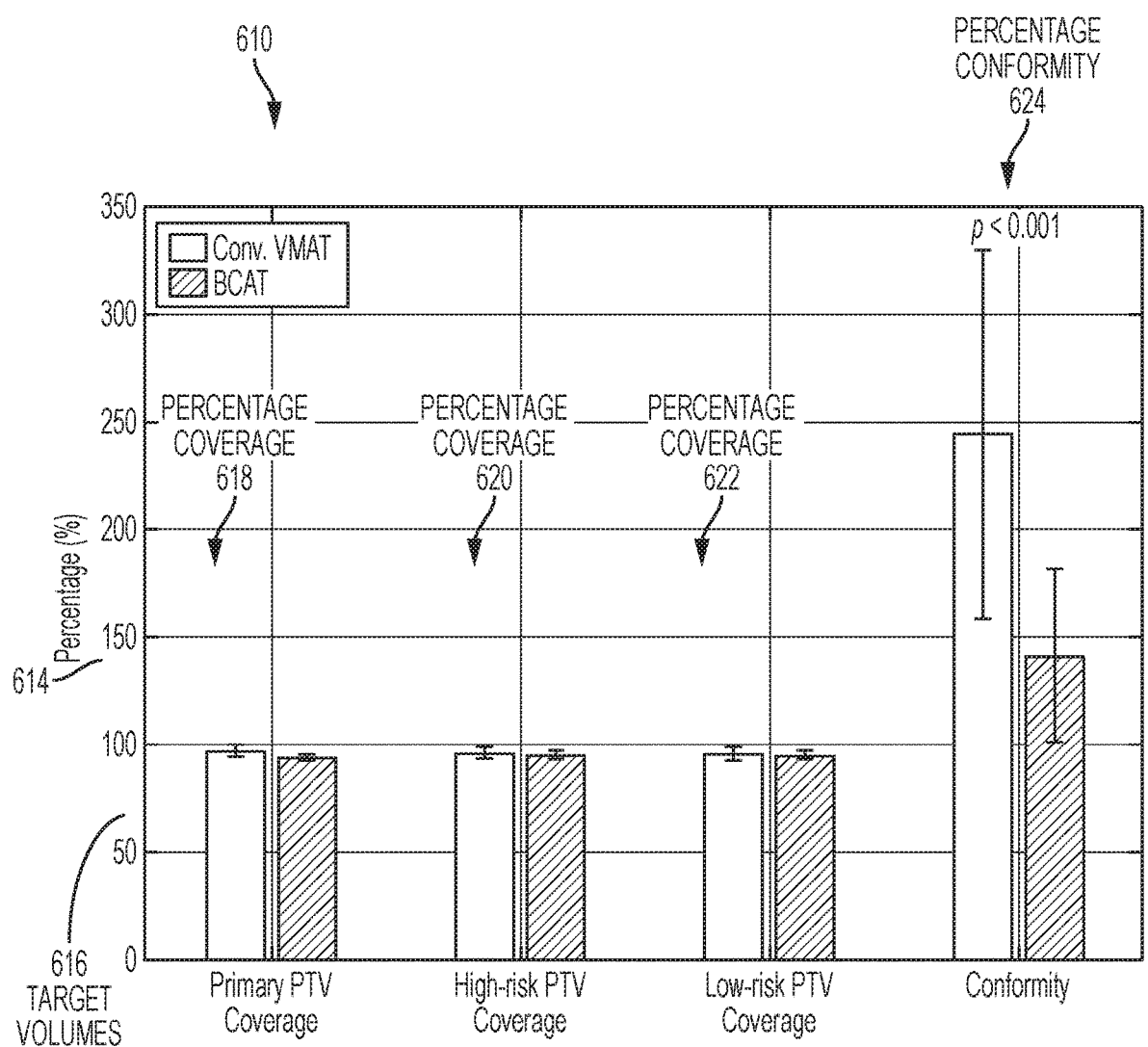
FIG. 6B is a graph that illustrates an example of coverage and conformity of target volumes, according to an embodiment.

In some embodiments, step 503 is performed to determine one or more apertures 211 at a plurality of therapy angles, where the number of apertures 211 at each therapy angle do not exceed a predetermined maximum number of apertures. In one embodiment, in step 503 the user is prompted to input the number of therapy angles and the maximum number of apertures at each therapy angle. In one example embodiment, one or more apertures 211 are determined for respective arcs, e.g., 3, 5 and 8 therapy angles per arc, such that the apertures 211 do not exceed 5 apertures at each therapy angle (each case can be noted as s3-n5, s5-n5 and s8-n5, respectively, where s3 indicates 3 therapy angles, s5 indicates 5 therapy angles, s8 indicates 8 therapy angles, and n5 indicates a maximum of 5 apertures per therapy angle). In one embodiment, in step 510, a new aperture is determined at one or more of the therapy angles. In some embodiments, the gantry speed is zero at one or more therapy angles. In other embodiments, the gantry speed is small but non-zero at one or more therapy angles. In these embodiments, increasing the number of therapy angles generally improved the quality of the dosimetric plan quality. However, in some embodiments that consider delivery efficiency, 3 or 4 therapy angles were sufficient. FIG. 6H is a graph 690 that illustrates an example of treatment times of various treatment plans, according to an embodiment. The horizontal axis 692 indicates different treatment plans including the three BCAT plans (e.g. s3-n5, s5-n5, s8-n5) and a conventional VMAT plan (labeled "clinical"). The vertical axis 694 indicates treatment time in units of seconds (s). In an example embodiment, the treatment time 695 of the conventional VMAT ("Clinical") plan is about 190 seconds, the treatment time 696 of the s3-n5 plan is about 143 seconds, the treatment time 697 of the s5-n5 plan is about 157 seconds and the treatment time 698 of the s8-n5 plan is about 226 seconds. The graph 690 compares the delivery efficiency of treatment time (e.g. mean±standard deviation) between typical clinical 2-arc VMAT and the s3-n5, s4-n5 and s8-n5 plans. Clearly, the s3-n5 treatment plan is superior in terms of efficiency, being delivered in less time 696 than any other treatment plan.

In some embodiments, step 503 is performed to determine the initial beam intensity at each angle in the arc. In these embodiments, the upper bound of the beam intensity value is 10 monitor units/second (MU/sec). In these embodiments, the lower bound of the beam intensity value is 0 monitor units/second (MU/sec). In these embodiments, the maximum variation of the beam intensity value between adjacent angles is 2 monitor units/second (MU/sec).

In some embodiments, step 504 is performed for more than one volume of target material 192, such that the upper bound and lower bound of the objective function 410 associated with equation (1) is set for each volume of target material 192. In an example embodiment, step 504 is performed for one or more of a primary target volume, a high-risk target volume and a low-risk target volume. In this example embodiment, the method is used to treat locally advanced head and neck cancer chances, such as oropharynx, nasopharynx, larynx and hypopharynx. In this example embodiment, the respective prescription dose $PD_t$ in equation (1) for the primary target volume, high-risk target volume and low-risk target volume is 70 Gray (Gy), 59.4 Gy and 54 Gy. In an example embodiment, the upper bound and lower bound for the dose $PD_t$ of the primary target volume is 77 Gy and 70 Gy, respectively. In an example embodiment, the upper bound and lower bound for the dose $PD_t$ of the high-risk target volume is 65 Gy and 59.4 Gy, respectively. In an example embodiment, the upper bound and lower bound for the dose $PD_t$ of the low-risk target volume is 59.4 Gy and 54 Gy, respectively.

In some embodiments, step 504 is also performed for more than one OAR 194, such that the upper bound and lower bound of the objective function 412 associated with equation (2) is set for each OAR 194. In an example embodiment, step 504 is performed for one or more of a left parotid, a right parotid and an oral cavity. In this example embodiment, the respective upper and lower bounds of the mean dose expressed in equation (2) for the left and right parotids is 20 Gy and 26 Gy, respectively. In this example embodiment, the upper and lower bounds of the mean dose expressed in equation (2) for the oral cavity is 35 Gy and 40 Gy, respectively.

In some embodiments, step 504 is also performed for more than one critical organ 195, such that the upper bound and lower bound of the objective function 414 associated with equation (3) is set for each critical organ 195. In an example embodiment, step 504 is performed for a spinal cord and/or a brain stem. In this example embodiment, the upper and lower bounds of the maximum dose expressed in equation (3) for the spinal cord is 40 Gy and 45 Gy, respectively. In this example embodiment, the upper and lower bounds of the maximum dose expressed in equation (3) for the brain stem is 50 Gy and 54 Gy, respectively.

In some embodiments, step 504 is also performed for normal tissue, such that the upper bound and lower bound of the objective function 414 associated with equation (4) is set for the normal tissue. In an example embodiment, the upper and lower bounds of the maximum dose expressed in equation (4) for the normal tissue is 70 Gy and 80 Gy, respectively.

In some embodiments, step 508 is performed by determining the aperture rate of change constraint expressed in equation (9) using the angular increment ($\delta_i$) between the angles and the gantry speed or angular rate of change values ($v_i$) from step 503. Additionally, in some embodiments, the aperture rate of change constraint expressed in equation (9) is further determined by using the adjustment speed values v of the metal leaves 212 from step 503 to determine the adjustment time expressed in equation (10). In other embodiments, step 508 is performed by using the angular rate of change values from step 503 to establish the angular rate of change constraint expressed in equation (11). In other embodiments, step 508 is performed by setting the minimum percentage α, in the constraint of equation (18) at 95%.

To show the efficacy of the approach described herein, after the beam is delivered at the plurality of therapy angles in step 518 using the aperture and beam intensity values at each angle, a comparison is made between the dose distribution of this BCAT plan and a conventional VMAT plan. FIG. 6B is a graph 610 that illustrates an example of coverage and conformity of target volumes, according to an embodiment. The horizontal axis 616 indicates the various target volume statistics, including the primary target volume, the high-risk target volume and the low-risk target volume and conformity. The vertical axis 614 indicates a percentage value that indicates one of a coverage percentage of the target volume receiving the prescription dose $PD_t$ or a conformity percentage of the target volume, defined below. The coverage percentage is defined as a percentage of the target volume that receives the prescription dose $PD_t$. The conformity percentage is defined as a ratio of a total volume that receives the prescription dose $PD_t$ (e.g., inside or outside of the target volume) to a volume of the target volume. Unlike the coverage percentage, which has a maximum value of 100%, the conformity percentage can exceed 100%. However, an ideal value of the conformity percentage is 100%, so to confine the prescription dose $PD_t$ within the target volume.

The percentage coverage 618 for the primary target volume, the percentage coverage 620 for the high-risk target volume and the percentage coverage 622 for the low-risk target volume is substantially similar for the BCAT (right bar in each statistic) and conventional VMAT plans (left bar in each case). However, the percentage conformity 624 for the BCAT plan is much closer to 100% than the conventional VMAT plan and thus the BCAT plan is much improved over the conventional VMAT plan. In an example embodiment, the percentage conformity 624 for the s3-n5, s5-n5 and s8-n5 BCAT plans is about 152%, 149% and 149% respectively, whereas the percentage conformity for the conventional VMAT plan is about 244%.

Figure 6C:
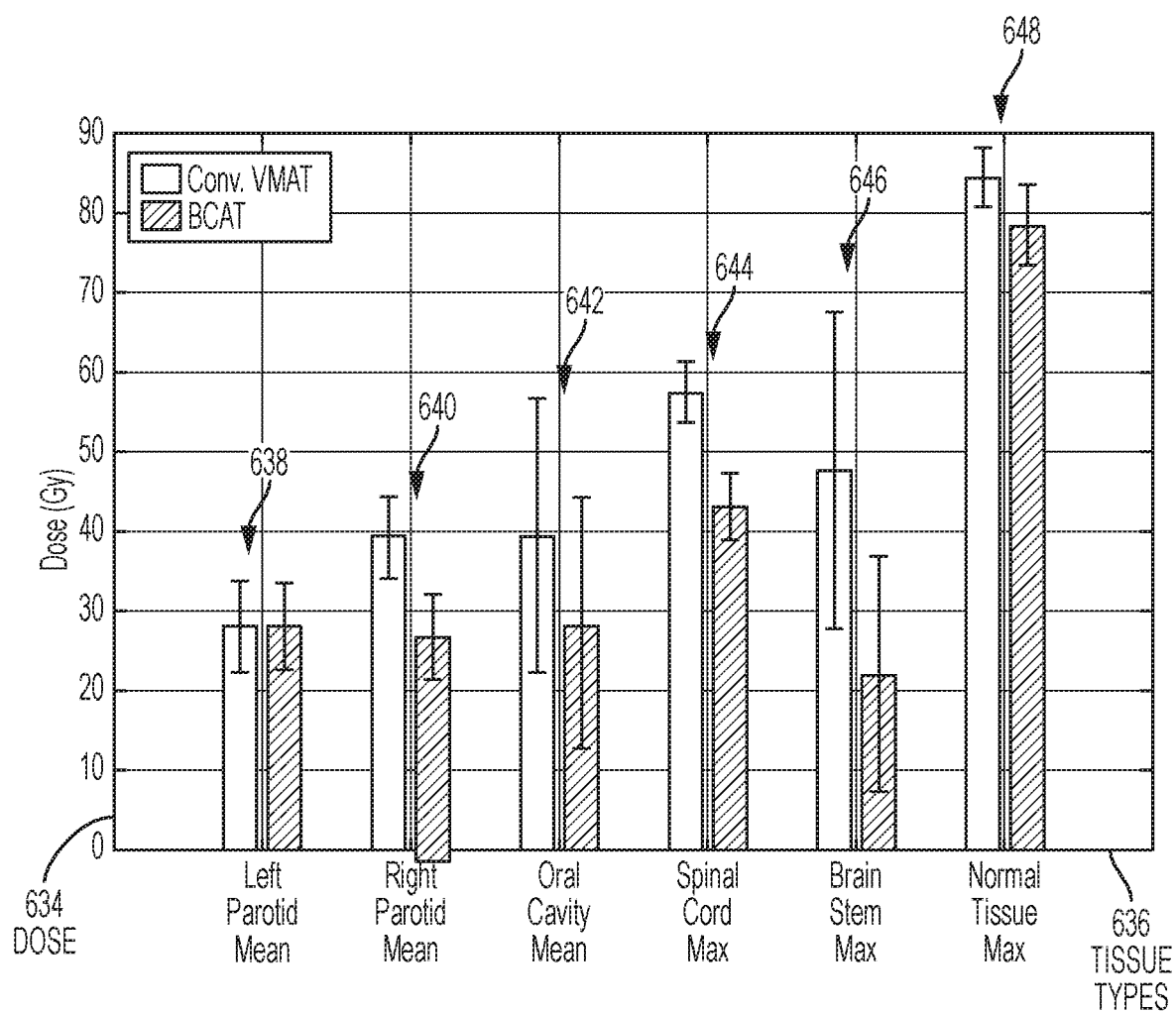
FIG. 6C is a graph that illustrates an example of mean and max dosages of organs-at-risk, critical organ and normal tissue, according to an embodiment.

FIG. 6C is a graph 630 that illustrates an example of mean and max dosages of organs-at-risk, critical organ and normal tissue, according to an embodiment. The horizontal axis 636 indicates the various tissue type statistics, with the VMAT values given by the left bar and the BCAT values given by the right bar for each statistic. In an example embodiment, the BCAT values are based on the s3-n5, s5-n5 or s8-n5 BCAT plans. The vertical axis 634 indicates the dose received at each tissue type in units of Gray (Gy). The left parotid mean dose 638 is approximately equal between the BCAT and conventional VMAT plans. The right parotid mean dose 640 is approximately 32% lower in the BCAT plan than the conventional VMAT plan. The oral cavity mean dose 642 is approximately 28% lower in the BCAT plan than the conventional VMAT plan. In other embodiments, the oral cavity mean dose 642 is approximately 38% lower in the BCAT plan than the conventional VMAT plan. The spinal cord maximum dose 644 is approximately 24.8% lower in the BCAT plan than the conventional VMAT plan. In other embodiments, the spinal cord maximum dose 644 is approximately 34% lower in the BCAT plan than the conventional VMAT plan. The brain stem maximum dose 646 is approximately 58.6% lower in the BCAT plan than the conventional VMAT plan. The normal tissue maximum dose 648 is approximately 7% lower in the BCAT plan than the conventional VMAT plan. Thus, with the exception of the left parotid OAR, each OAR, critical organ and normal tissue in the BCAT plan advantageously received a noticeably reduced dose relative to the conventional VMAT plan.

FIG. 6D is a graph 650 that illustrates an example of fractional volume versus dosage for a primary target volume, the right parotid OAR and the brain stem, according to an embodiment. The horizontal axis 652 indicates the dose received in units of Gray (Gy). The vertical axis 654 indicates the fractional volume (unitless). Two curves and corresponding shaded regions representing plus and minus one standard deviation is shown for each of the primary target volume, the right parotid OAR and the brain stem. The upper curve for each tissue type indicates the conventional VMAT plan and the lower curve indicates the BCAT plan. As can be seen, the BCAT plan delivers much lower doses to the non target tissues (up to about 20 Gy lower), while essentially the same dose to 98% of the primary target tissue. In an example embodiment, FIG. 6D illustrates that at least 95% target coverage was achieved for the s3-n5, s5-n5 and s8-n5 plans.

FIG. 6E is a graph 660 that illustrates an example of fractional volume versus dosage for a high-risk target volume and the left parotid OAR, according to an embodiment. The horizontal axis 662 indicates the dose received in units of Gray (Gy). The vertical axis 664 indicates the fractional volume (unitless). Two curves and corresponding shaded regions representing plus and minus one standard deviation is shown for each of the high-risk target volume (as in FIG. 6D) and the left parotid OAR. The lower curve for the left parotid type indicates the conventional VMAT plan and the upper curve indicates the BCAT plan. The upper curve for the high risk primary target type indicates the conventional VMAT plan and the lower curve indicates the BCAT plan. As can be seen, the BCAT plan delivers only slightly higher doses to the left parotid (about 5 Gy or less), while essentially the same dose to 98% of the high risk primary target tissue.

Figure 6F:
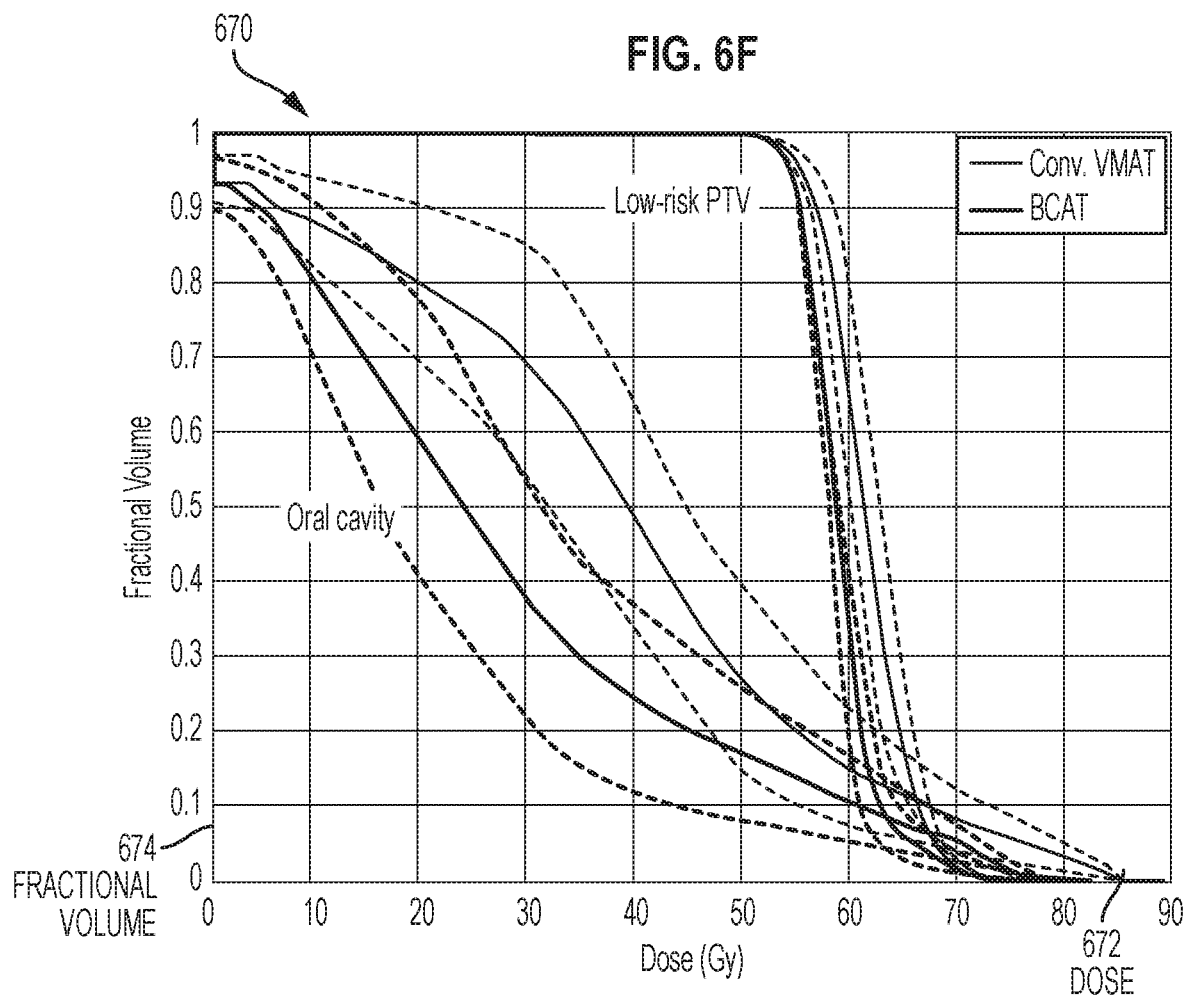
FIG. 6F is a graph that illustrates an example of fractional volume versus dosage for a target volume and an organ-at-risk, according to an embodiment.

FIG. 6F is a graph 670 that illustrates an example of fractional volume versus dosage for a low-risk target volume and the oral cavity OAR, according to an embodiment. The horizontal axis 672 indicates the dose received in units of Gray (Gy). The vertical axis 674 indicates the fractional volume (unitless). Two curves and corresponding shaded regions representing plus and minus one standard deviation are shown for each of the low-risk target volume and the oral cavity OAR. The upper curve for each tissue type indicates the conventional VMAT plan and the lower curve indicates the BCAT plan. As can be seen, the BCAT plan delivers much lower doses to the oral cavity (almost 20 Gy), while essentially the same dose to 98% of the low risk primary target tissue.

Figure 6G:
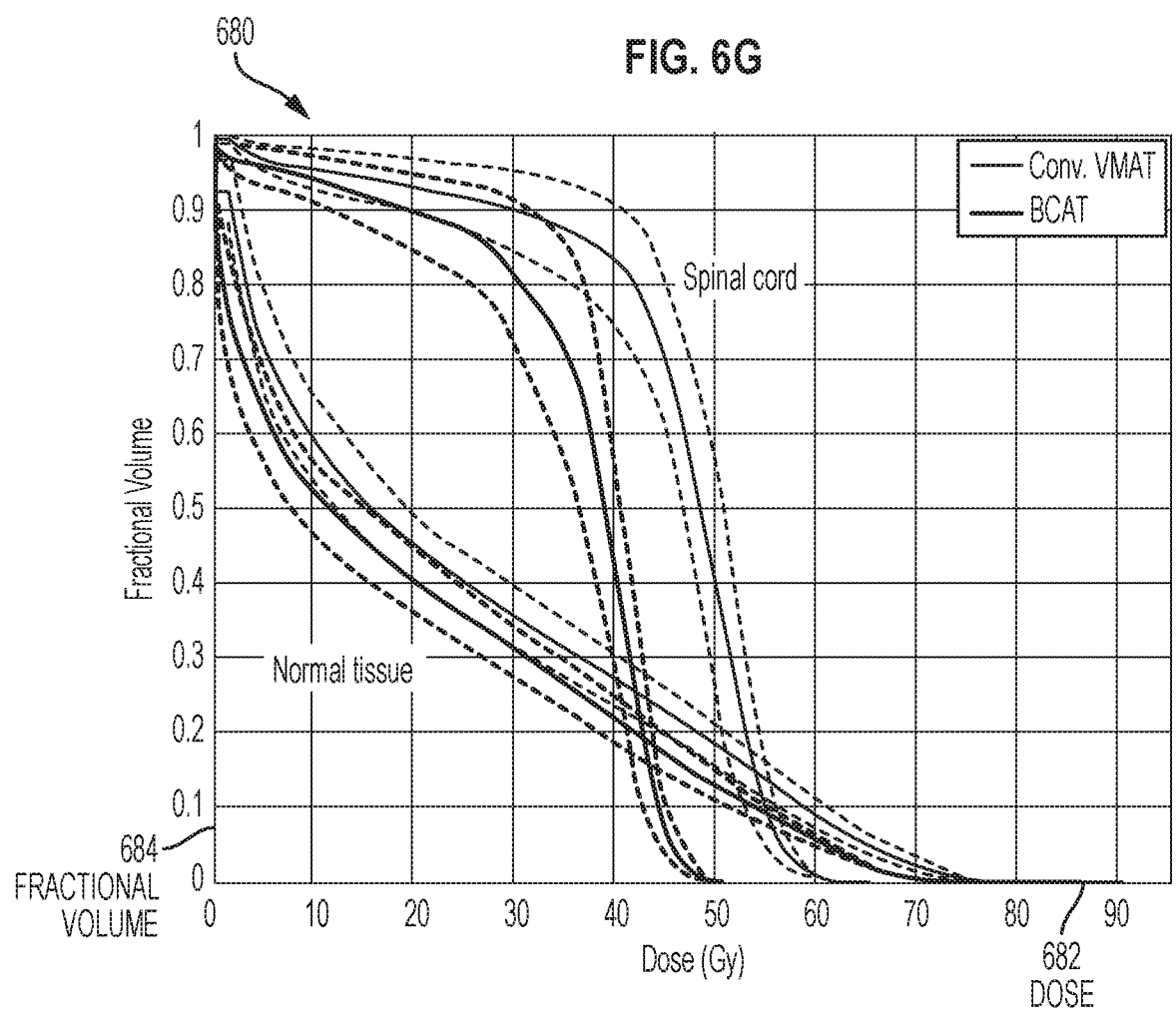
FIG. 6G is a graph that illustrates an example of fractional volume versus dosage for a target volume and an organ-at-risk, according to an embodiment.
Figure 6H:
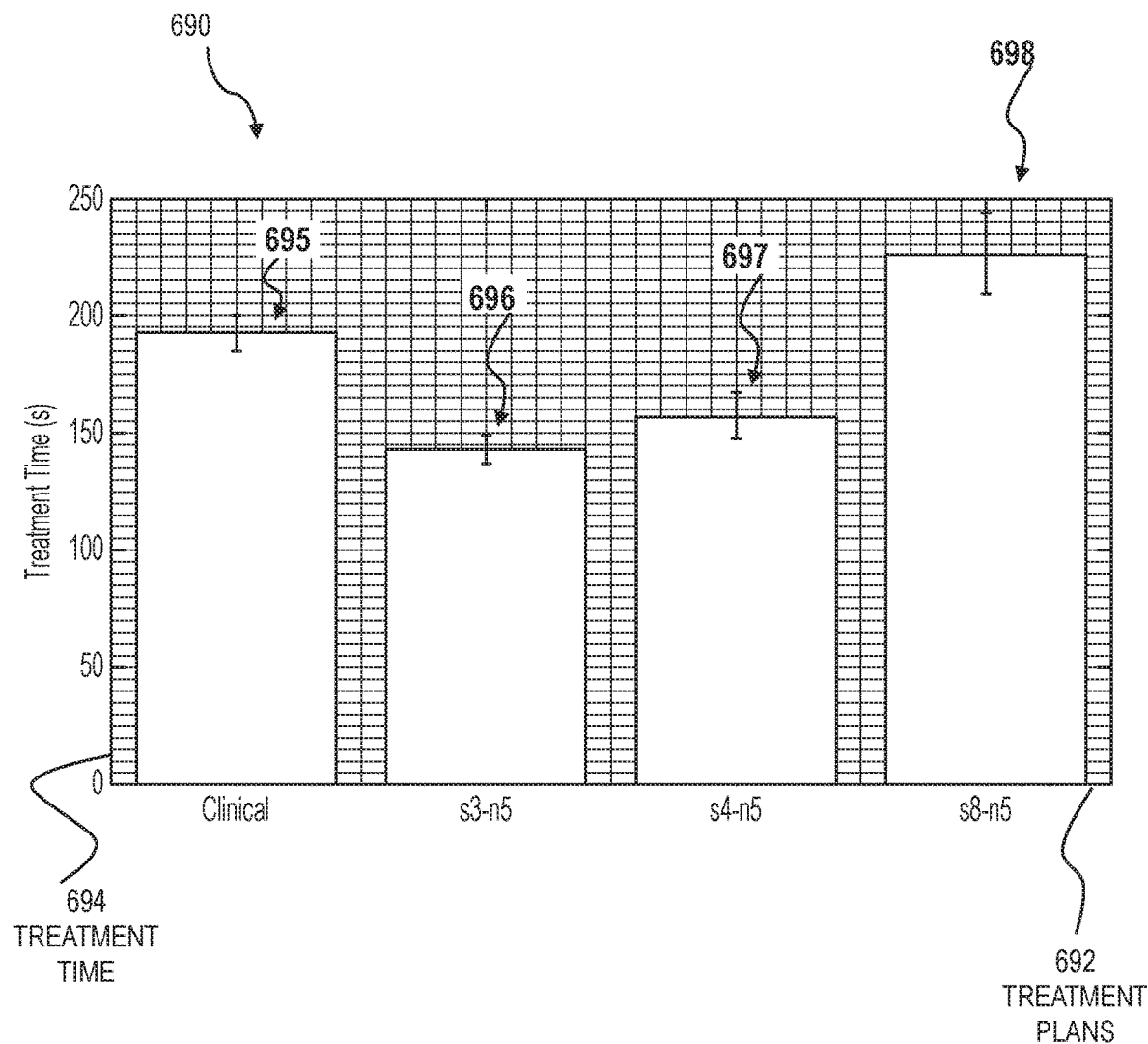
FIG. 6H is a graph that illustrates an example of treatment times of various treatment plans, according to an embodiment.

FIG. 6G is a graph 680 that illustrates an example of fractional volume versus dosage for spinal cord OAR and normal tissue, according to an embodiment. The horizontal axis 682 indicates the dose received in units of Gray (Gy). The vertical axis 684 indicates the fractional volume (unitless). Two curves and corresponding shaded regions representing plus and minus one standard deviation are shown for each of the spinal cord OAR and normal tissue. The upper curve for each tissue type indicates the conventional VMAT plan and the lower curve indicates the BCAT plan. As can be seen, the BCAT plan delivers much lower doses (about 10 Gy lower) to the spinal cord OAR, while delivering somewhat lower doses (about 5 Gy lower) to the normal tissue.

The graphs of FIGS. 6D-6G indicate that both of the BCAT and conventional VMAT plans provide sufficient coverage (e.g. 95%) for all three of the target volumes. Additionally, the BCAT plan outperformed the conventional VMAT plan with respect to OAR, critical organ and normal tissue sparing. Additionally, the BCAT plan provides a more uniform dose (e.g. percentage conformity closer to 100%) to the target volume than the conventional VMAT plan.

3. Hardware Overview

FIG. 7 is a block diagram that illustrates a computer system 700 upon which an embodiment of the invention may be implemented. Computer system 700 includes a communication mechanism such as a bus 710 for passing information between other internal and external components of the computer system 700. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 700, or a portion thereof, constitutes a means for performing one or more steps of one or more methods described herein.

A sequence of binary digits constitutes digital data that is used to represent a number or code for a character. A bus 710 includes many parallel conductors of information so that information is transferred quickly among devices coupled to the bus 710. One or more processors 702 for processing information are coupled with the bus 710. A processor 702 performs a set of operations on information. The set of operations include bringing information in from the bus 710 and placing information on the bus 710. The set of operations also typically include comparing two or more units of information, shifting positions of units of information, and combining two or more units of information, such as by addition or multiplication. A sequence of operations to be executed by the processor 702 constitutes computer instructions.

Computer system 700 also includes a memory 704 coupled to bus 710. The memory 704, such as a random access memory (RAM) or other dynamic storage device, stores information including computer instructions. Dynamic memory allows information stored therein to be changed by the computer system 700. RAM allows a unit of information stored at a location called a memory address to be stored and retrieved independently of information at neighboring addresses. The memory 704 is also used by the processor 702 to store temporary values during execution of computer instructions. The computer system 700 also includes a read only memory (ROM) 706 or other static storage device coupled to the bus 710 for storing static information, including instructions, that is not changed by the computer system 700. Also coupled to bus 710 is a non-volatile (persistent) storage device 708, such as a magnetic disk or optical disk, for storing information, including instructions, that persists even when the computer system 700 is turned off or otherwise loses power.

Information, including instructions, is provided to the bus 710 for use by the processor from an external input device 712, such as a keyboard containing alphanumeric keys operated by a human user, or a sensor. A sensor detects conditions in its vicinity and transforms those detections into signals compatible with the signals used to represent information in computer system 700. Other external devices coupled to bus 710, used primarily for interacting with humans, include a display device 714, such as a cathode ray tube (CRT) or a liquid crystal display (LCD), for presenting images, and a pointing device 716, such as a mouse or a trackball or cursor direction keys, for controlling a position of a small cursor image presented on the display 714 and issuing commands associated with graphical elements presented on the display 714.

In the illustrated embodiment, special purpose hardware, such as an application specific integrated circuit (IC) 720, is coupled to bus 710. The special purpose hardware is configured to perform operations not performed by processor 702 quickly enough for special purposes. Examples of application specific ICs include graphics accelerator cards for generating images for display 714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 700 also includes one or more instances of a communications interface 770 coupled to bus 710. Communication interface 770 provides a two-way communication coupling to a variety of external devices that operate with their own processors, such as printers, scanners and external disks. In general the coupling is with a network link 778 that is connected to a local network 780 to which a variety of external devices with their own processors are connected. For example, communication interface 770 may be a parallel port or a serial port or a universal serial bus (USB) port on a personal computer. In some embodiments, communications interface 770 is an integrated services digital network (ISDN) card or a digital subscriber line (DSL) card or a telephone modem that provides an information communication connection to a corresponding type of telephone line. In some embodiments, a communication interface 770 is a cable modem that converts signals on bus 710 into signals for a communication connection over a coaxial cable or into optical signals for a communication connection over a fiber optic cable. As another example, communications interface 770 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 770 sends and receives electrical, acoustic or electromagnetic signals, including infrared and optical signals, that carry information streams, such as digital data.

The term computer-readable medium is used herein to refer to any medium that participates in providing information to processor 702, including instructions for execution. Such a medium may take many forms, including, but not limited to, non-volatile media, volatile media and transmission media. Non-volatile media include, for example, optical or magnetic disks, such as storage device 708. Volatile media include, for example, dynamic memory 704. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 702, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 702, except for carrier waves and other signals.

Logic encoded in one or more tangible media includes one or both of processor instructions on a computer-readable storage media and special purpose hardware, such as ASIC *720.

Network link 778 typically provides information communication through one or more networks to other devices that use or process the information. For example, network link 778 may provide a connection through local network 780 to a host computer 782 or to equipment 784 operated by an Internet Service Provider (ISP). ISP equipment 784 in turn provides data communication services through the public, world-wide packet-switching communication network of networks now commonly referred to as the Internet 790. A computer called a server 792 connected to the Internet provides a service in response to information received over the Internet. For example, server 792 provides information representing video data for presentation at display 714.

The invention is related to the use of computer system 700 for implementing the techniques described herein. According to one embodiment of the invention, those techniques are performed by computer system 700 in response to processor 702 executing one or more sequences of one or more instructions contained in memory 704. Such instructions, also called software and program code, may be read into memory 704 from another computer-readable medium such as storage device 708. Execution of the sequences of instructions contained in memory 704 causes processor 702 to perform the method steps described herein. In alternative embodiments, hardware, such as application specific integrated circuit 720, may be used in place of or in combination with software to implement the invention. Thus, embodiments of the invention are not limited to any specific combination of hardware and software.

The signals transmitted over network link 778 and other networks through communications interface 770, carry information to and from computer system 700. Computer system 700 can send and receive information, including program code, through the networks 780, 790 among others, through network link 778 and communications interface 770. In an example using the Internet 790, a server 792 transmits program code for a particular application, requested by a message sent from computer 700, through Internet 790, ISP equipment 784, local network 780 and communications interface 770. The received code may be executed by processor 702 as it is received, or may be stored in storage device 708 or other non-volatile storage for later execution, or both. In this manner, computer system 700 may obtain application program code in the form of a signal on a carrier wave.

Various forms of computer readable media may be involved in carrying one or more sequence of instructions or data or both to processor 702 for execution. For example, instructions and data may initially be carried on a magnetic disk of a remote computer such as host 782. The remote computer loads the instructions and data into its dynamic memory and sends the instructions and data over a telephone line using a modem. A modem local to the computer system 700 receives the instructions and data on a telephone line and uses an infra-red transmitter to convert the instructions and data to a signal on an infra-red a carrier wave serving as the network link 778. An infrared detector serving as communications interface 770 receives the instructions and data carried in the infrared signal and places information representing the instructions and data onto bus 710. Bus 710 carries the information to memory 704 from which processor 702 retrieves and executes the instructions using some of the data sent with the instructions. The instructions and data received in memory 704 may optionally be stored on storage device 708, either before or after execution by the processor 702.

FIG. 8 illustrates a chip set 800 upon which an embodiment of the invention may be implemented. Chip set 800 is programmed to perform one or more steps of a method described herein and includes, for instance, the processor and memory components described with respect to FIG. 7 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 800, or a portion thereof, constitutes a means for performing one or more steps of a method described herein.

In one embodiment, the chip set 800 includes a communication mechanism such as a bus 801 for passing information among the components of the chip set 800. A processor 803 has connectivity to the bus 801 to execute instructions and process information stored in, for example, a memory 805. The processor 803 may include one or more processing cores with each core configured to perform independently. A multi-core processor enables multiprocessing within a single physical package. Examples of a multi-core processor include two, four, eight, or greater numbers of processing cores. Alternatively or in addition, the processor 803 may include one or more microprocessors configured in tandem via the bus 801 to enable independent execution of instructions, pipelining, and multithreading. The processor 803 may also be accompanied with one or more specialized components to perform certain processing functions and tasks such as one or more digital signal processors (DSP) 807, or one or more application-specific integrated circuits (ASIC) 809. A DSP 807 typically is configured to process real-world signals (e.g., sound) in real time independently of the processor 803. Similarly, an ASIC 809 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 803 and accompanying components have connectivity to the memory 805 via the bus 801. The memory 805 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 805 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

What is claimed is:

1. A method comprising:
    determining a plurality of voxels in a reference frame of a radiation source that rotates at an angular rate of change based on a gantry speed and emits a beam of radiation at a plurality of angles with controlled intensity based on a beam intensity value and beam cross sectional shape at each angle based on a value of an aperture of a collimator positioned between the radiation source and a subject;
    determining an initial aperture at each angle;
    minimizing a single objective function subject to a constraint on an aperture rate of change based on an adjustment speed of the collimator using the initial aperture and an initial beam intensity value at each of the plurality of angles to determine the beam intensity and aperture at each angle;
    delivering the beam of radiation with controlled intensity and beam cross sectional shape at each angle based on the beam intensity and the aperture; and
    turning the beam of radiation off at an intervening angle not included in the plurality of angles;
    wherein the determining the initial aperture at each angle is based on the aperture value at an adjacent angle, the angular rate of change between the angle and the adjacent angle and the aperture rate of change.

2. A method as recited in claim 1, wherein the minimizing of the single objective function is further subject to a constraint on the angular rate of change.

3. A method as recited in claim 2, wherein the minimizing of the single objective function is further subject to a constraint on the beam intensity, a constraint on a variation of the angular rate of change between consecutive angles, and a constraint on a variation of the beam intensity between consecutive angles.

4. A method as recited in claim 1, wherein the constraint on the aperture rate of change is a minimum adjustment speed of the collimator such that an adjustment time of the collimator between apertures at consecutive angles is less than or equal to a rotation time of the radiation source between the consecutive angles.

5. A method as recited in claim 4, wherein the collimator is a multi-leaf collimator (MLC), wherein the value of the aperture is adjusted by moving metal leaves along rows within the MLC at the adjustment speed;
    wherein the adjustment time of the collimator between the apertures is a ratio of a maximum displacement of the metal leaves within the MLC between the apertures to the adjustment speed of the metal leaves within the MLC;
    and wherein the rotation time of the radiation source is a ratio of an angular spacing between the consecutive angles to the angular rate of change between the consecutive angles.

6. A method as recited in claim 1, wherein the minimizing the single objective function is to further determine a radiation dose delivered to the voxels, and wherein the method further comprises:
    determining for a new angle other than the plurality of angles an aperture and a beam intensity value based on the radiation dose delivered to the voxels; and
    minimizing the single objective function subject to the constraint on the aperture rate of change and a constraint on the angular rate of change using the apertures and beam intensity values at the plurality of angles and the new angle such that the value of the single objective function is reduced from the value of the single objective function determined from the minimizing the single objective function using the plurality of angles without the new angle;
    wherein delivering the beam of radiation with controlled intensity and beam cross sectional shape at each angle using the beam intensity and the aperture comprises delivering the beam of radiation with controlled intensity and beam cross sectional shape at each angle including the new angle using the beam intensity and the aperture.

7. A method as recited in claim 6 wherein the determining the aperture for the new angle comprises:
    determining a rotation time of the radiation source from the new angle to an adjacent angle among the plurality of angles, based on an angular spacing between the new angle and the adjacent angle and the angular rate of change between the adjacent angle and the new angle;
    determining an adjustment time of the collimator from the aperture at the adjacent angle to the aperture at the new angle based on the aperture rate of change; and
    selecting the aperture for the new angle such that the adjustment time is less than or equal to the rotation time.

8. A method as recited in claim 1, further comprising:
    setting an upper and lower bound on a plurality of objective functions associated with a plurality of tissue types within the subject;
    wherein the single objective is based on the plurality of objective functions and the upper and lower bound of each objective function;
    and wherein the minimizing the single objective function is to further determine a radiation dose delivered to the voxels of each tissue type.

9. A method as recited in claim 8 wherein the plurality of tissue types includes a target tissue type and wherein the minimizing of the single objective function is subject to a constraint that a prescription dose is delivered to a minimum percentage of the target tissue type.

10. A method as recited in claim 8 further comprising defining parameters based on the upper and lower bound for each objective function, wherein the parameters are used to define the single objective function and wherein the parameters include the upper bound and a reciprocal of a difference between the upper and lower bound.

11. A method as recited in claim 1, wherein the delivering the beam of radiation comprises varying the gantry speed of the radiation source at one or more of the plurality of angles.

12. A method as recited in claim 1, wherein the beam intensity value is zero at one or more of the plurality of angles.

13. A method as recited in claim 1, wherein the delivering the beam of radiation at each angle comprises delivering the beam of radiation over an angular range centered on each angle.

14. A method as recited in claim 1, further comprising:
    determining a second aperture and a second beam intensity value at each angle of a second plurality of angles over a negative arc of the radiation source around the subject;

wherein the minimizing and the delivering steps are further performed based on the second apertures and second beam intensity values.

15. A method as recited in claim 1 wherein the delivering the beam of radiation comprises continuously rotating the radiation source at a fixed gantry speed throughout the arc.

16. A method as recited in claim 1 further comprising determining the initial beam intensity value at each angle based on the beam intensity value at the adjacent angle, a maximum variation of the beam intensity from the adjacent angle to the angle, a lower bound of the beam intensity and an upper bound of the beam intensity.

17. A method as recited in claim 1 wherein the determining the initial aperture at the angle comprises:
   determining a rotation time of the radiation source from the adjacent angle to the angle based on an angular spacing between the angle and the adjacent angle and the angular rate of change between the adjacent angle and the angle;
   determining an adjustment time of the collimator from the aperture at the adjacent angle to the initial aperture at the angle based on the aperture rate of change; and
   selecting the initial aperture such that the adjustment time is less than or equal to the rotation time.

18. A method as recited in claim 17 wherein the collimator is a multi-leaf collimator (MLC), wherein the value of the aperture is adjusted by moving metal leaves along rows within the MLC at the adjustment speed and wherein the determining of the adjustment time of the MLC comprises;
   determining a maximum displacement of the metal leaves within the MLC from the aperture at the adjacent angle to the initial aperture at the angle; and
   calculating the adjustment time based on a ratio of the maximum displacement to the adjustment speed of the metal leaves within the MLC.

19. A method as recited in claim 1 wherein the radiation source is one of an X-ray Computed tomography (CT) scanner or an nuclear magnetic resonance imagery (MRI) scanner.

20. A computer-readable medium carrying one or more sequences of instructions, wherein execution of the one or more sequences of instructions by one or more processors causes the one or more processors to perform the steps of:
   determining a plurality of voxels in a reference frame of a radiation source that rotates at an angular rate of change based on a gantry speed and emits a beam of radiation at a plurality of angles with controlled intensity based on a beam intensity value and with beam cross sectional shape at each angle based on a value of an aperture of a collimator positioned between the radiation source and a subject;
   determining an initial aperture at each angle;
   minimizing a single objective function subject to a constraint on an aperture rate of change based on an adjustment speed of the collimator and a constraint on the angular rate of change using the initial aperture and an initial beam intensity value at each of the plurality of angles to determine the beam intensity and aperture at each angle;
   delivering the beam of radiation with controlled intensity and beam cross sectional shape at each angle based on the beam intensity and the aperture; and
   turn the beam of radiation off at an intervening angle not included in the plurality of angles;
   wherein the determining the initial aperture at each angle is based on the aperture value at an adjacent angle, the angular rate of change between the angle and the adjacent angle and the aperture rate of change.

21. A computer-readable medium as recited in claim 20, wherein the minimizing the single objective function is to further a radiation dose delivered to the voxels and wherein execution of the one or more sequences of instructions by one or more processors further causes the one or more processors to perform the steps of:
   determining for a new angle other than the plurality of angles an aperture and a beam intensity value based on the radiation dose delivered to the voxels; and
   minimizing the single objective function subject to the constraint on the aperture rate of change and the constraint on the angular rate of change using the apertures and beam intensity values at the plurality of angles and the new angle such that the value of the single objective function is reduced from the value of the single objective function determined from the minimizing of the single objective function using the plurality of angles without the new angle;
   wherein delivering the beam of radiation with controlled intensity and beam cross sectional shape at each angle using the beam intensity and the aperture comprises delivering the beam of radiation with controlled intensity and beam cross sectional shape at each angle including the new angle using the beam intensity and the aperture.

22. A system comprising:
   a radiation source configured to rotate at an angular rate of change based on a gantry speed to emit a beam of radiation with controlled intensity based on a beam intensity value at a plurality of angles to each voxel of a plurality of voxels comprising a reference frame of the radiation source;
   a collimator positioned between the radiation source and a subject;
   an aperture with a value at each angle defined by the collimator to control a cross sectional shape of the beam of radiation at each voxel in the reference frame;
   at least one processor; and
   at least one memory including one or more sequence of instructions;
   the at least one memory and the one or more sequence of instructions configured to, with the at least one processor, cause the at least one processor to;
   determine an initial aperture at each angle;
   minimize a single objective function subject to a constraint on an aperture rate of change based on an adjustment speed of the collimator and a constraint on the angular rate of change using the initial aperture and an initial beam intensity value at each of the plurality of angles to determine the beam intensity and aperture at each angle;
   deliver the beam of radiation with controlled intensity and beam cross sectional shape at each angle based on the beam intensity and the aperture; and
   turn the beam of radiation off at an intervening angle not included in the plurality of angles;
   wherein the initial aperture at each angle is determined based on the aperture value at an adjacent angle, the angular rate of change between the angle and the adjacent angle and the aperture rate of change.

23. A system as recited in claim 22, wherein the minimization of the single objective function is to further determine a radiation dose delivered to the voxels and wherein the at least one memory and the one or more sequence of instructions are configured to, with the at least one processor, further cause the at least one processor to:

determine for a new angle other than the plurality of angles an aperture and a beam intensity value based on the radiation dose delivered to the voxels; and minimize the single objective function subject to the constraint on the aperture rate of change and the constraint on the angular rate of change using the apertures and beam intensity values at the plurality of angles and the new angle such that the value of the single objective function is reduced from the value of the single objective function determined from the minimizing of the single objective function using the plurality of angles without the new angle;

wherein delivery of the beam of radiation with controlled intensity and beam cross sectional shape at each angle using the beam intensity and the aperture comprises delivery of the beam of radiation with controlled intensity and beam cross sectional shape at each angle including the new angle using the beam intensity and the aperture.

24. A system as recited in claim 22, wherein the collimator is a multi-leaf collimator (MLC) positioned between the radiation source and the subject, including leaves configured to move within rows at the adjustment speed to adjust the value of the aperture at each angle;

and wherein the determination of the initial aperture at the angle is further based on a maximum displacement of the metal leaves within the MLC from the aperture at the adjacent angle to the initial aperture at the angle and the adjustment speed of the metal leaves within the MLC.

25. A system as recited in claim 22 wherein the radiation source is one of an X-ray Computed tomography (CT) scanner or an nuclear magnetic resonance imagery (MRI) scanner.

* * * * *